United States Patent
Savari et al.

(10) Patent No.: US 10,514,324 B2
(45) Date of Patent: Dec. 24, 2019

(54) METHODS RELATING TO DESIGNING WELLBORE STRENGTHENING FLUIDS

(71) Applicant: Halliburton Energy Services, Inc., Houston, TX (US)

(72) Inventors: Sharath Savari, Houston, TX (US); Arunesh Kumar, Feltham (GB); Jason T. Scorsone, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 90 days.

(21) Appl. No.: 15/177,684

(22) Filed: Jun. 9, 2016

(65) Prior Publication Data

US 2016/0282234 A1    Sep. 29, 2016

Related U.S. Application Data

(62) Division of application No. 13/546,060, filed on Jul. 11, 2012, now Pat. No. 9,388,333.

(51) Int. Cl.
*C09K 8/42* (2006.01)
*E21B 21/00* (2006.01)
(Continued)

(52) U.S. Cl.
CPC .............. *G01M 99/008* (2013.01); *C09K 8/03* (2013.01); *C09K 8/426* (2013.01); *C09K 8/502* (2013.01);
(Continued)

(58) Field of Classification Search
CPC .................................................... E21B 21/003
(Continued)

(56) References Cited

U.S. PATENT DOCUMENTS 4,447,340 A    5/1984    Fed
4,807,469 A    2/1989    Hall
(Continued)

FOREIGN PATENT DOCUMENTS

WO          0194742 A1    12/2001
WO    WO 2005/121198 A1   12/2005
(Continued)

OTHER PUBLICATIONS

Kefi, et al.; IADC/SPE 133735, Optimizing in Four Steps Composite Lost-Circulation Pills Without Knowing Loss Zone Width; IADC/SPE Asia Pacific Drilling Technology Conference and Exhibition held in Ho Chi Minh City, Vietnam, Nov. 2010.
(Continued)

*Primary Examiner* — Taras P Bemko
(74) *Attorney, Agent, or Firm* — Tenley Krueger; C. Tumey Law Group PLLC

(57) ABSTRACT

Generally, assessing the properties of a plug comprising wellbore strengthening materials may enable the design of more efficient wellbore strengthening additives and fluids because the properties of the plug may translate to the near wellbore strengthening effect of the wellbore strengthening materials of the plug. Assessing such properties may involve applying a differential pressure to a plug formed in a passageway of a tool comprising at least one sensor proximal to the passageway plug, and then measuring at least one attribute selected from the group consisting of a normal plug pressure, a normal plug displacement, and any combination thereof with the at least one sensor.

14 Claims, 20 Drawing Sheets

(51) Int. Cl.
  *G01M 99/00* (2011.01)
  *C09K 8/03* (2006.01)
  *C09K 8/502* (2006.01)
  *C09K 8/504* (2006.01)
  *G01N 11/04* (2006.01)

(52) U.S. Cl.
  CPC .......... *C09K 8/504* (2013.01); *C09K 2208/08* (2013.01); *E21B 21/003* (2013.01); *G01N 11/04* (2013.01)

(58) Field of Classification Search
  USPC .................................................. 166/250.04
  See application file for complete search history.

(56) References Cited

U.S. PATENT DOCUMENTS

| | | |
|---|---|---|
| 4,957,174 A | 9/1990 | Whitfall et al. |
| 5,023,005 A | 6/1991 | Thaler et al. |
| 5,284,207 A | 2/1994 | Bittleston et al. |
| 5,770,805 A | 6/1998 | Castel |
| 5,783,822 A | 7/1998 | Buchanan et al. |
| 5,826,669 A | 10/1998 | Zaleski et al. |
| 5,905,061 A | 5/1999 | Patel |
| 5,977,031 A | 11/1999 | Patel |
| 6,058,544 A | 7/2000 | Palmer et al. |
| 6,164,380 A | 12/2000 | Davis |
| 6,220,350 B1 | 4/2001 | Brothers et al. |
| 6,290,001 B1 * | 9/2001 | West .................. C09K 8/05 175/61 |
| 6,584,833 B1 | 7/2003 | Jamiston et al. |
| 6,630,429 B1 | 10/2003 | Cremeans et al. |
| 6,659,175 B2 | 12/2003 | Malone et al. |
| 6,725,926 B2 | 4/2004 | Nguyen et al. |
| 6,828,279 B2 | 12/2004 | Patel et al. |
| 7,066,285 B2 | 6/2006 | Shaarpour |
| 7,264,053 B2 | 9/2007 | Vargo, Jr. et al. |
| 7,331,391 B2 | 2/2008 | Keese et al. |
| 7,456,135 B2 | 11/2008 | Kirsner et al. |
| 7,462,580 B2 | 12/2008 | Kirsner et al. |
| 7,488,704 B2 | 2/2009 | Kirsner et al. |
| 7,507,692 B2 | 3/2009 | Xiang |
| 7,534,743 B2 | 5/2009 | Kirsner et al. |
| 7,547,663 B2 | 6/2009 | Kirsner et al. |
| 7,696,131 B2 | 4/2010 | Oyler et al. |
| 7,776,797 B2 | 8/2010 | Allin et al. |
| 2004/0231845 A1 | 11/2004 | Cooke |
| 2006/0178275 A1 | 8/2006 | Shaarpour |
| 2006/0237192 A1 | 10/2006 | Shaarpour |
| 2007/0017675 A1 | 1/2007 | Hammami et al. |
| 2007/0017676 A1 | 1/2007 | Reddy et al. |
| 2007/0169937 A1 | 7/2007 | Allin et al. |
| 2008/0060811 A1 | 3/2008 | Bour et al. |
| 2008/0236891 A1 | 10/2008 | Huynh et al. |
| 2010/0018294 A1 | 1/2010 | Tonmukayakul et al. |
| 2010/0088078 A1 | 4/2010 | Geehan et al. |
| 2010/0101146 A1 | 4/2010 | Fujimori et al. |
| 2010/0139387 A1 | 6/2010 | Jamison et al. |
| 2010/0152070 A1 | 6/2010 | Ghassemzadeh |
| 2010/0193184 A1 | 8/2010 | Dolman et al. |
| 2010/0224365 A1 * | 9/2010 | Abad .................. E21B 43/26 166/275 |
| 2010/0314108 A1 | 12/2010 | Crews et al. |

FOREIGN PATENT DOCUMENTS

| | | |
|---|---|---|
| WO | WO 2007/020436 A2 | 2/2007 |
| WO | WO 2009/106796 A1 | 9/2009 |
| WO | WO 2010/088484 A2 | 8/2010 |
| WO | WO 2010/133302 A1 | 11/2010 |
| WO | WO 2010/142370 A1 | 12/2010 |
| WO | WO 2014/011391 A2 | 1/2014 |

OTHER PUBLICATIONS

Van Vliet, et al.; OTC 7889, Development and Field Use of Fibre-Containing Cement; Offshore Technology Conference held in Houston, TX, pp. 183-197, May 1995.
Savari et al., Engineered Insight into "Unexplored" Lost Circulation Material (LCM) Properties Corroborating Wellbore Strengthening Phenomenon, IORS 2010.
Halliburton Brochure, Accolade® High-Performance Synthetic-Based Fluids from Baroid, The Leader in a Family of Award-Winning, Clay-Free Invert Emulsion-Based Fluids, 2007.
Halliburton Brochure, Hydro-Guard® Inhibitive Water-Based Fluid, A High Performance Solution for Reactive Formations and Environmentally Sensitive Locations, 2006.
Halliburton Brochure, Innovert® High Performance Paraffin/Mineral Oil-Based Fluids from Baroid, Completing the Circle: Award-Winning Accolade® Fluid Technology for Paraffin/Mineral Oil-Based Systems, 2007.
Kumar et al., Wellbore Strengthening: The Less-Studied Properties of Lost-Circulation Materials, SPE Annual Technical Conference and Exhibition held in Florence, Italy, Sep. 2010, SPE 133484.
Savari et al., Improved Lost Circulation Treatment Design and Testing Techniques Minimize Formation Damage, SPE European Formation Damage Conference held in Noordwijk, The Netherlands, Jun. 2011, SPE 143603.
Kumar et al., Application of Fiber Laden Pill for Controlling Lost Circulation in Natural Fractures, American Association of Drilling Engineers, 2011 AADE National Technical Conference and Exhibition held in Houston, Texas, AADE-11-NTCE-19.
Whitfall et al., "New Design Models and Materials Provide Engineered Solutions to Lost Circulation," 2006 SPE Russian Oil and Gas Technical Conference and Exhibition held in Moscow, Russia, Oct. 3-6, 2006, SPE 101693.
Whitfall et al., "Preventing Lost Circulation Requires Planning Ahead," 2007 International Oil Conference and Exhibition in Mexico held in Verzcruz, Mexico, Jun. 27-30, 2007, SPE 108647.
Whitfall, "Lost Circulation Material Selection, Particle Size Distribution and Fracture Modeling with Fracture Simulation Software," IAD/SPE Asia Pacific Drilling Technology Conference and Exhibition, 2008, IADC/SPE 115039.
Messier et al., Controlling Cement Tops Through Use of Fibre-Based Slurries Reduces Drilling Costs; JCPT Paper 2002-085TN, vol. 42, No. 5, May 2003.
Ravi et al., Cementing Technology for Low Fracture Gradient and Controlling Loss Circulation; SPE/IADC Indian Drilling Technology Conference and Exhibition, Mumbai, India, Oct. 2006, SPE/IADC 102074.
Aadnoy et al., Design of Well Barriers to Combat Circulation Losses; SPE/IADC Drilling Conference, Amsterdam, The Netherlands, Feb. 2007, SPE/IADC 105449.
Abe et al., Advances in Polymer Science, vol. 157, 2001.
Al-Awad, M.N., "Effect of Mud Filter Cake Efficiency on Wellbore Stability During Drilling Operations," Journal of Engineering and Applied Science, vol. 43, No. 5, Oct. 1996, pp. 1065-1076.
International Search Report and Written Opinion for PCT/US2013/047827 dated Jul. 23, 2014.
Baroid Fluid Services Brochure, "Engineered Wellsetim Treatment Service Helps Prevent Lost Circulation by Strengthening the Wellbore," 2007.
Song et al., "Preventing Mud Losses by Wellbore Strengthening," Society of Petroleum Engineers, 2006, SPE 101593.
Aston et al., "Drilling Fluids for Wellbore Strengthening," IADC/SPE Drilling Conference, 2004, IADC/SPE 87130.
Aston et al., "A New Treatment for Wellbore Strengthening in Shale," Society of Petroleum Engineers, 2007, SPE 110713.

\* cited by examiner

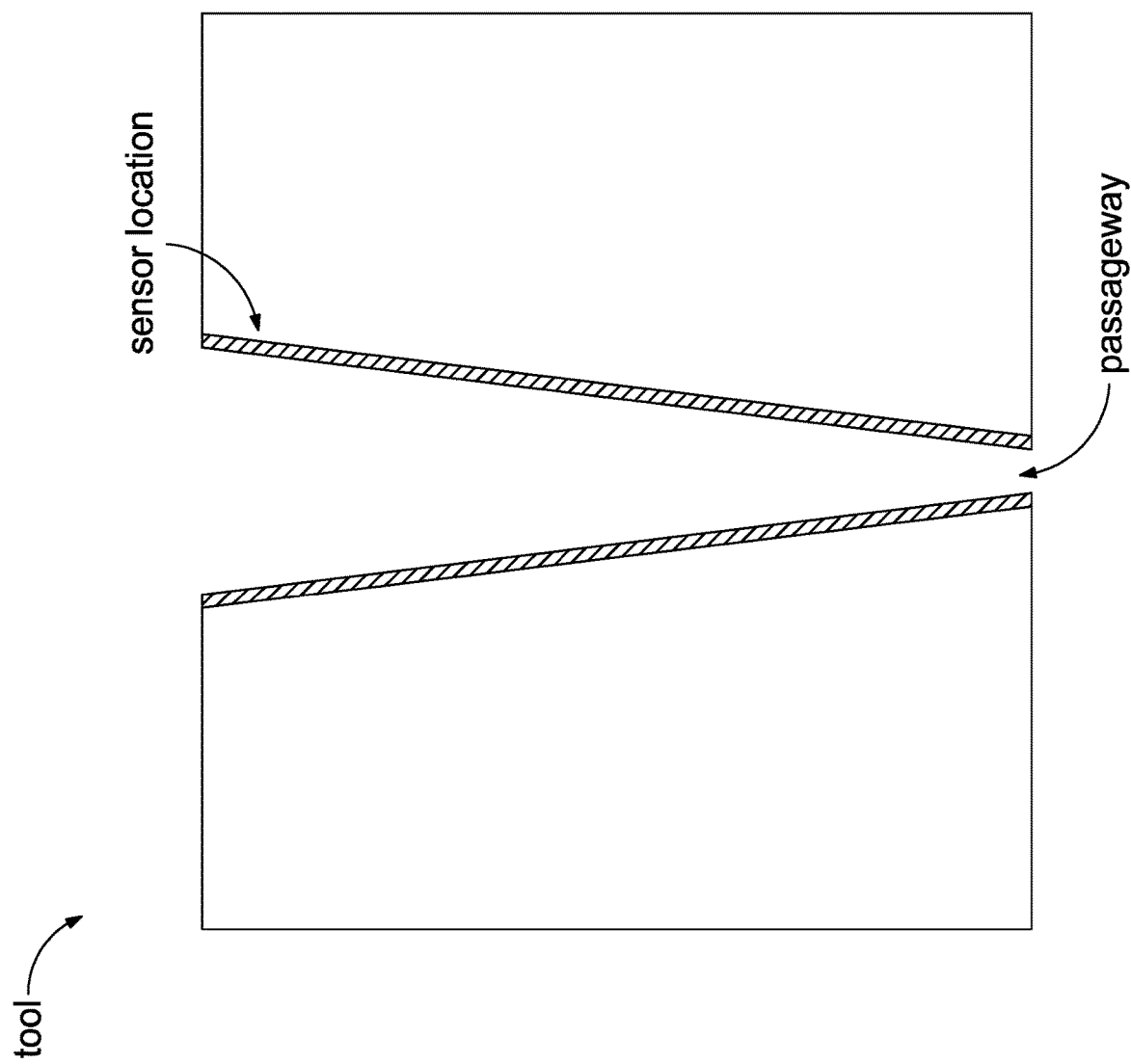

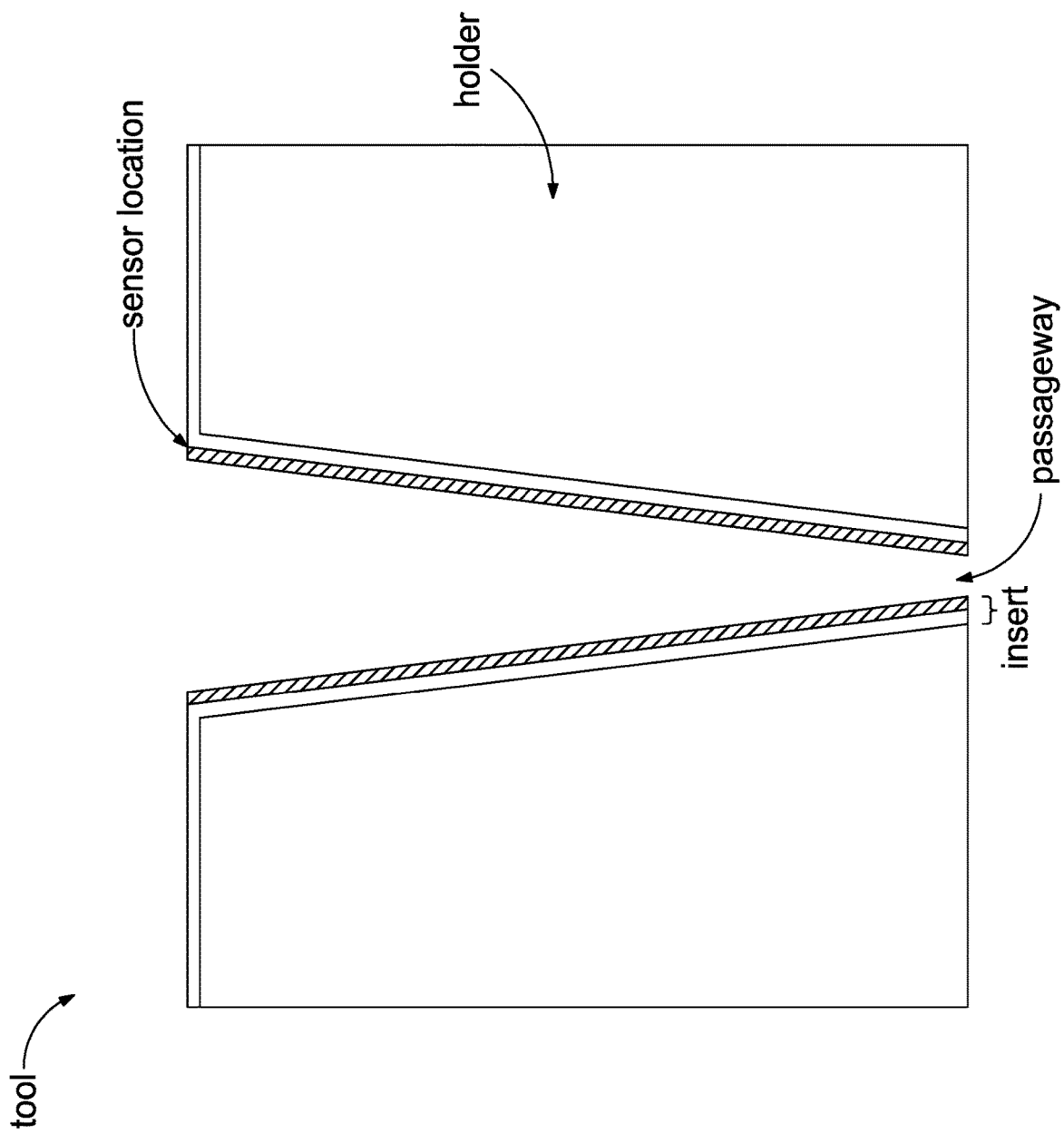

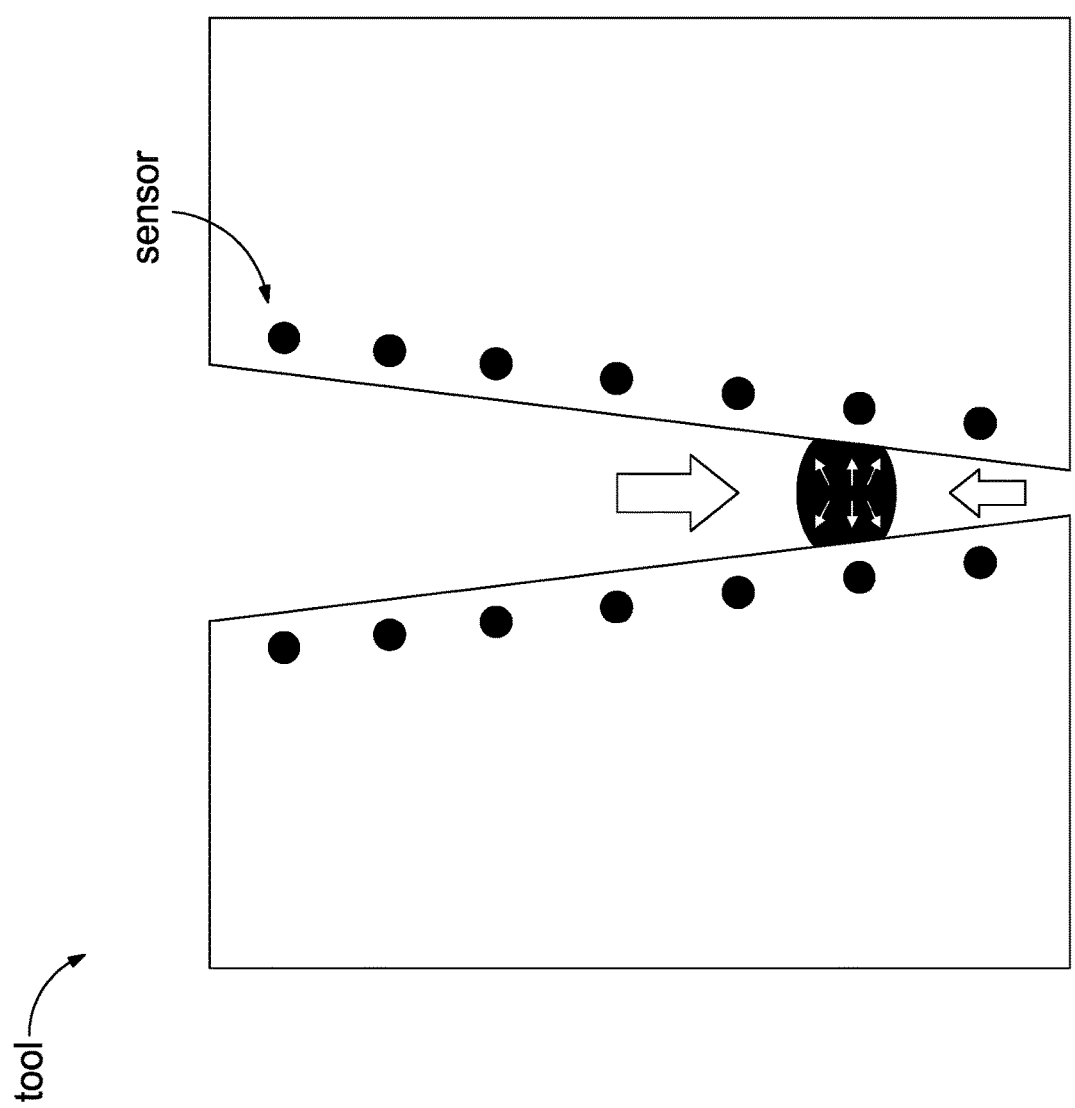

METHODS RELATING TO DESIGNING WELLBORE STRENGTHENING FLUIDS

BACKGROUND

The present invention relates to the design of wellbore strengthening additives and fluids based on the assessment of the properties of a plug comprising wellbore strengthening materials, including methods, apparatuses, and systems relating thereto. Generally, the properties of the plug may translate to the near wellbore strengthening effect of the wellbore strengthening materials of the plug.

Lost circulation is one of the larger contributors to non-productive drilling time. Lost circulation arises from drilling fluid leaking into the formation via undesired flow paths, e.g., permeable sections, natural fractures, and induced fractures. Lost circulation treatments may be used to remediate the wellbore by plugging the undesired flow paths before drilling can resume.

Drilling, most of the time, is performed with an overbalance pressure such that the wellbore pressure (equivalent circulating density) is maintained within the mud weight window, i.e., the area between the pore pressure (or collapse pressure) and the fracture pressure, see FIG. 1. That is, the pressure is maintained high enough to stop subterranean formation fluids from entering the wellbore and low enough to not create or unduly extend fractures surrounding the wellbore. The term "overbalance pressure," as used herein, refers to the amount of pressure in the wellbore that exceeds the pore pressure. The term "pore pressure," as used herein, refers to the pressure of fluids in the formation. Overbalance pressure is needed to prevent subterranean formation fluids from entering the wellbore. The term "fracture pressure," as used herein, refers to the pressure threshold where pressures exerted in excess of the fracture pressure from the wellbore onto the formation will cause one or more fractures in the subterranean formation. Wider mud weight windows allow for drilling with a reduced risk of lost circulation.

In traditional subterranean formations, the mud weight window may be wide, FIG. 1. However, in formations having problematic zones, e.g., depleted zones, high-permeability zones, highly tectonic areas with high in-situ stresses, or pressurized shale zones below salt layers, which are often found in formations with a plurality of lithographies, the mud weight window may be narrower and more variable, FIG. 2. When the overbalance pressure exceeds the fracture pressure, a fracture is expected to be induced, and lost circulation may occur. One proactive method of reducing the risk of lost circulation is to strengthen or stabilize the wellbore through the use of wellbore strengthening materials. One method of wellbore strengthening involves inducing fractures while simultaneously plugging the fractures. This simultaneous fracture-plug method increases the compressive tangential stress in the near-wellbore region of the subterranean formation, which translates to an increase in the fracture initiation pressure or fracture reopening pressure, thereby widening the mud weight window, FIG. 3. The extent of wellbore strengthening, i.e., expansion of the mud weight window, could be a function of the properties of the plug in terms of its ability to withstand higher pressures, among others as described in this invention. If the plug fails, lost circulation and drilling non-productive time results.

The strength of the plug may depend on, inter alia, keeping the induced fracture propped open and/or preserving the increased circumferential (hoop) stress that was required to open the fractures and/or isolating the fracture tips from the fluid and pressure of the wellbore. FIG. 4 provides an illustration of some of the downhole pressures relating to wellbore strengthening. FIG. 4 also illustrates isolation of the fracture tips from the wellbore by plugs comprising wellbore strengthening materials. Understanding how plugs comprising wellbore strengthening materials react to the various pressures experienced in a wellbore may advantageously allow for the design of wellbore strengthening fluids or additives thereof that better strengthen the wellbore, thereby minimizing fluid loss and consequently reducing rig downtime and costs.

SUMMARY OF THE INVENTION

The present invention relates to the design of wellbore strengthening additives and fluids based on the assessment of the properties of a plug comprising wellbore strengthening materials, including methods, apparatuses, and systems relating thereto. Generally, the properties of the plug may translate to the near wellbore strengthening effect of the wellbore strengthening materials of the plug.

In one embodiment of the present invention, a method may comprise: providing a fluid comprising a wellbore strengthening material; passing the fluid through a passageway of a tool comprising at least one sensor proximal to the passageway so as to form a plug that comprises the wellbore strengthening material in the passageway; applying a differential pressure to the plug in the passageway; and measuring at least one attribute selected from the group consisting of a normal plug pressure, a normal plug displacement, and any combination thereof with the at least one sensor.

In another embodiment of the present invention, a method may comprise: providing a first fluid comprising a first wellbore strengthening material; passing the first fluid through a passageway of a tool comprising at least one sensor proximal to the passageway so as to form a plug that comprises the first wellbore strengthening material in the passageway; applying a differential pressure to the plug in the passageway; measuring at least one attribute selected from the group consisting of a normal plug pressure, a normal plug displacement, and any combination thereof with the at least one sensor; deriving at least one value selected from the group consisting of sustained increased hoop stress, compressive strength of the plug, shear strength of the plug, and any combination thereof from the at least one attribute; and developing a wellbore strengthening additive comprising a second wellbore strengthening material based on the at least one value.

In yet another embodiment of the present invention, a tool may comprise an implement that comprises at least one passageway that models an opening in a subterranean formation, the passageway comprising an entry port on a first end of the object, an exit port at an opposing end of an object, and a wall extending from the entry port to the exit port; and at least one sensor in or on the implement proximal to the wall of the passageway.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combi

FIGS. 6A-E provide cross-sectional illustrations of nonlimiting examples of tool/sensor configurations.

FIG. 8A provides a nonlimiting illustration of a plug exerting a normal plug pressure on a passageway of a tool having sensors.

DETAILED DESCRIPTION

Figure 1:
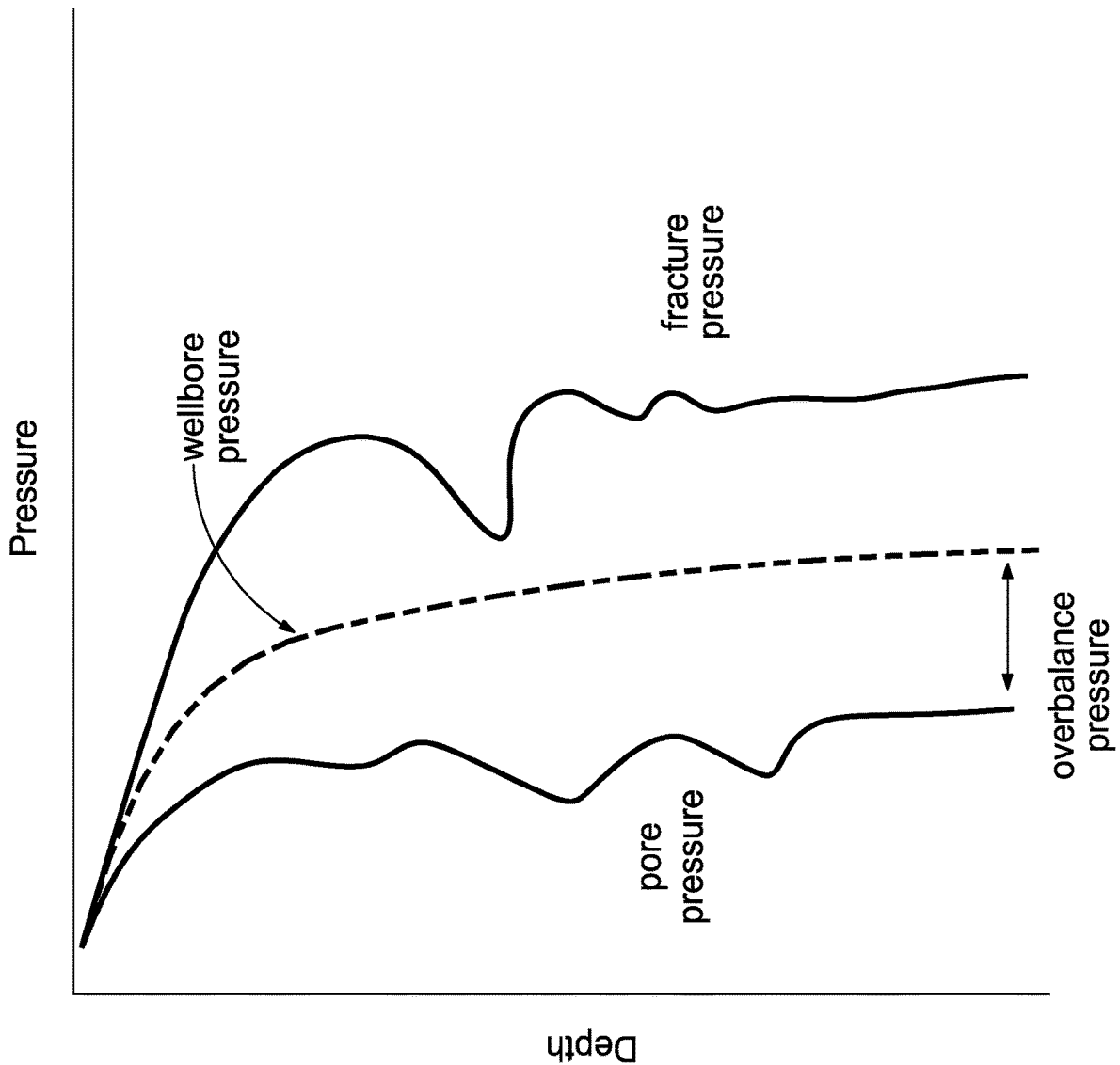
- FIG. 1 illustrates the mud weight window for a traditional wellbore.
Figure 2:
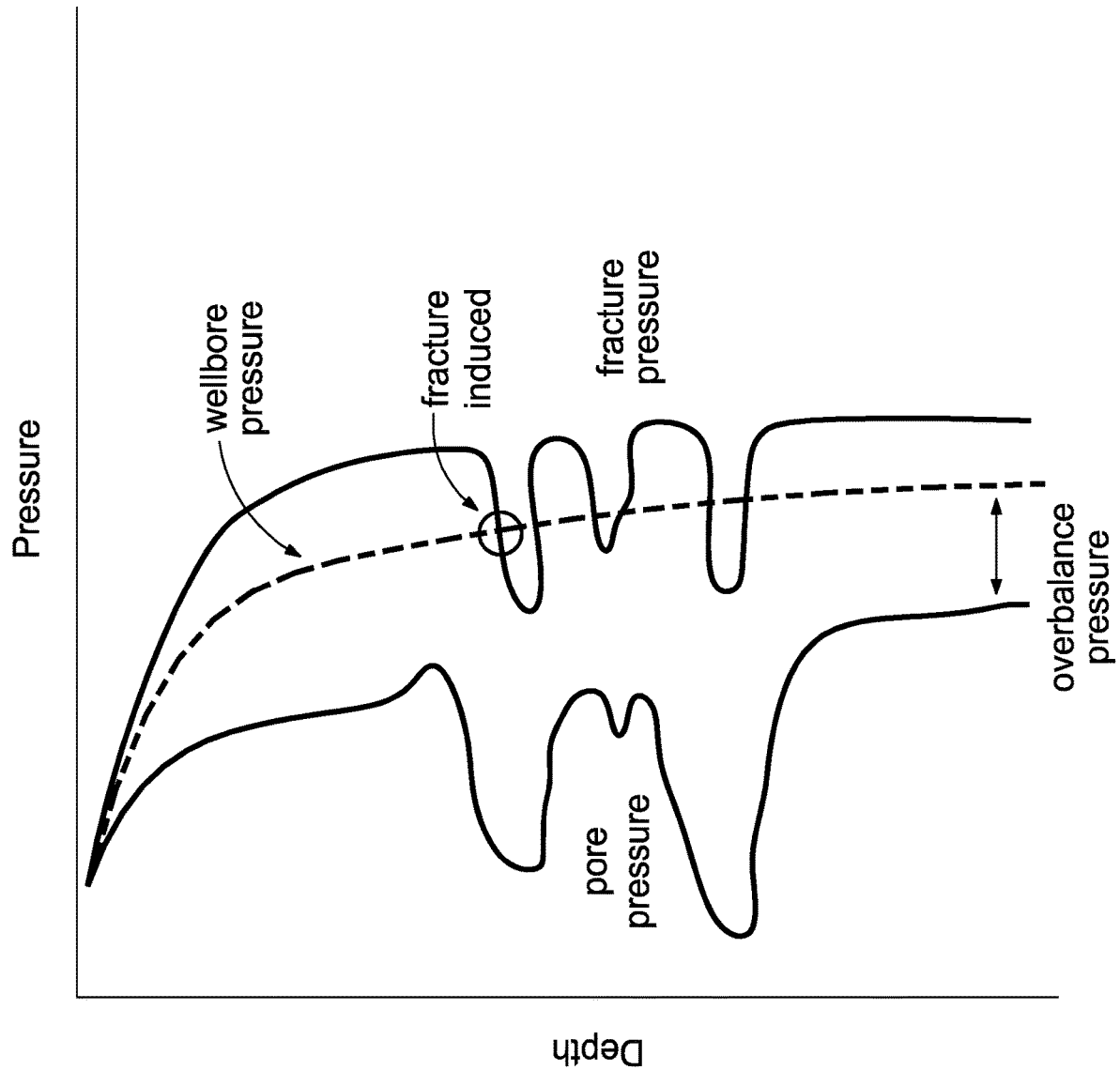
FIG. 2 illustrates the mud weight window for a problematic wellbore.
Figure 3:
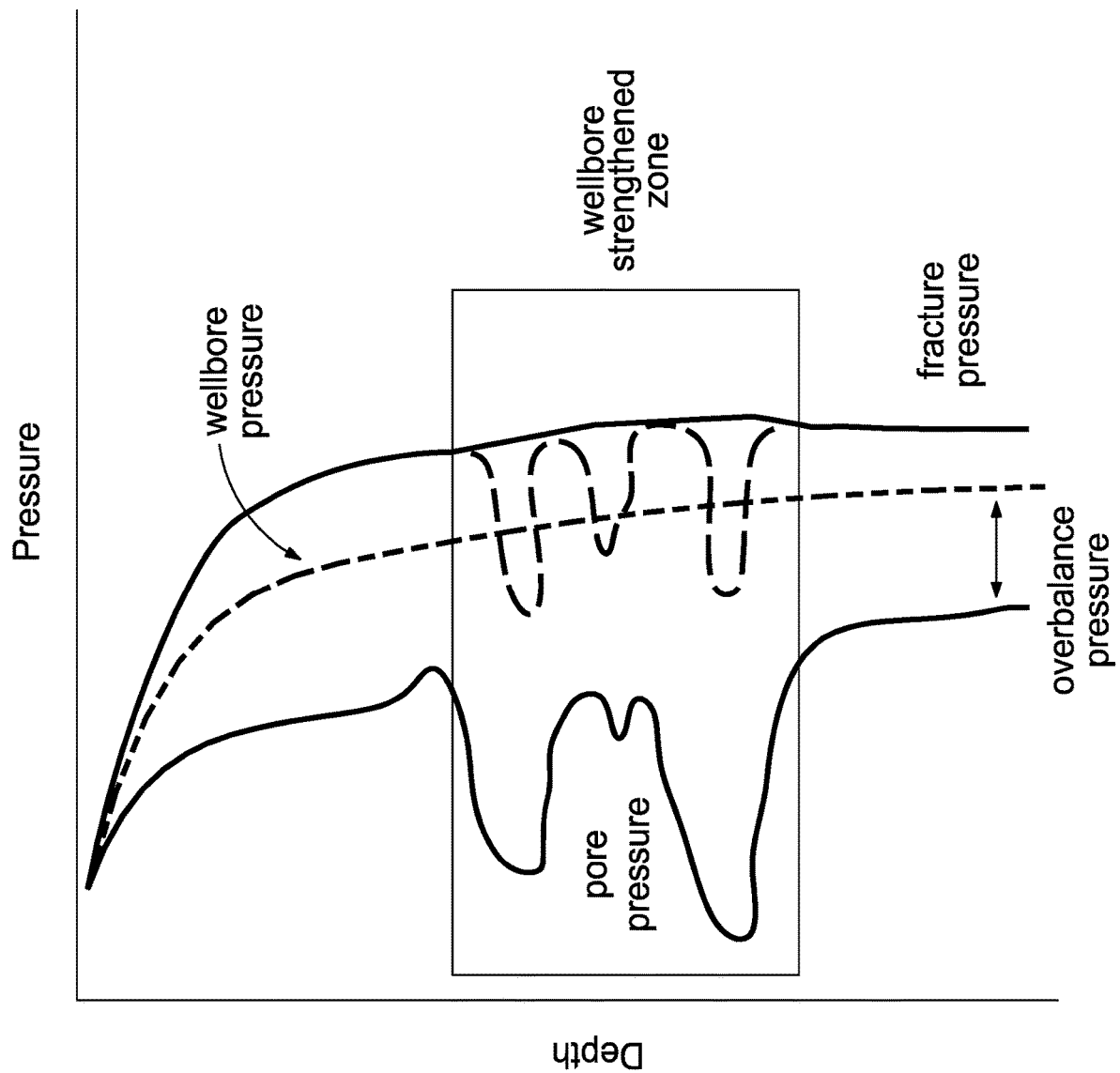
FIG. 3 illustrates the mud weight window for a strengthened wellbore.
Figure 4:
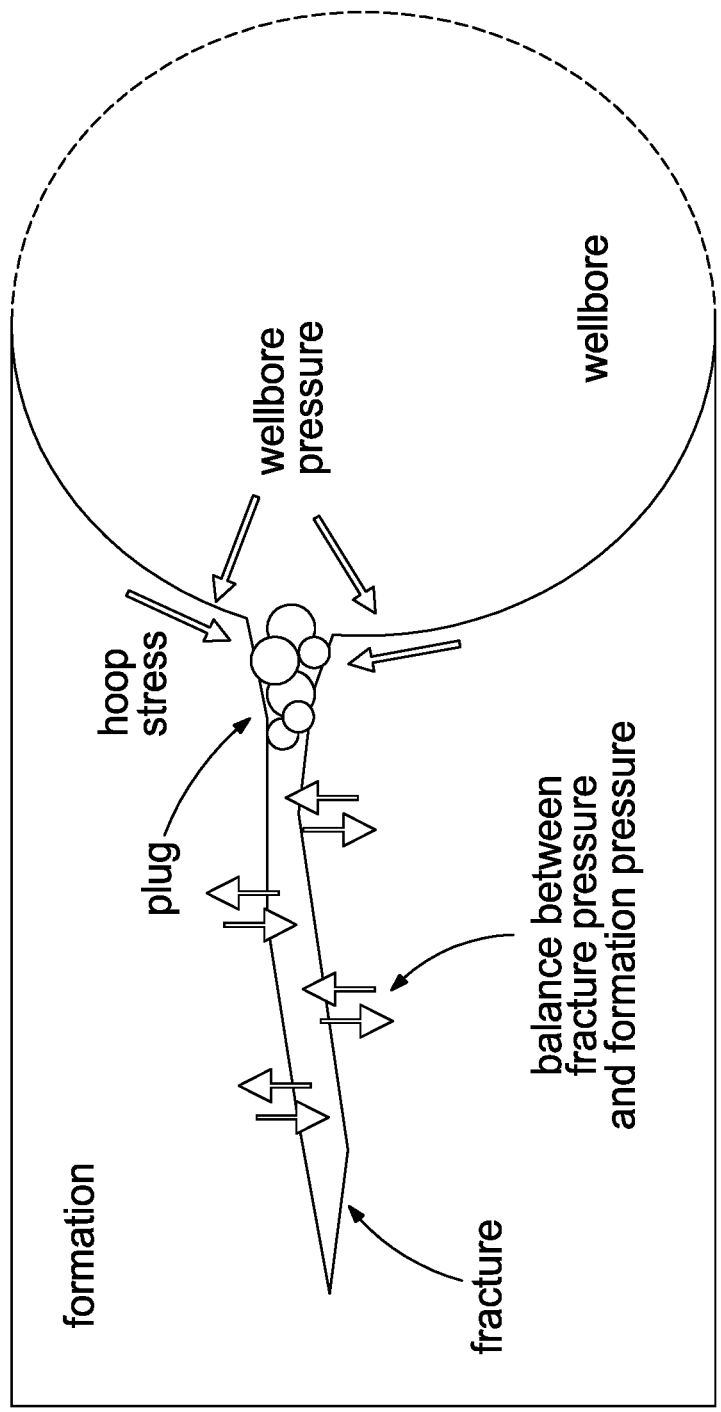
FIG. 4 illustrates some of the downhole pressures relating to wellbore strengthening.

The present invention relates to the design of wellbore strengthening additives and fluids based on the assessment of the properties of a plug comprising wellbore strengthening materials, including methods, apparatuses, and systems relating thereto. Generally, the properties of the plug may translate to the near wellbore strengthening effect of the wellbore strengthening materials of the plug.

The present invention provides for, in some embodiments, systems and apparatuses for assessing the wellbore strengthening capabilities of wellbore strengthening materials (WSM). By better understanding the characteristics and capabilities of individual WSM and/or combinations of WSM, wellbore strengthening fluids could be designed to provide improved wellbore strengthening, e.g., a greater or sustained increase in the mud weight window with stronger plugs of WSM and fluids and additives that achieve mud weight window expansions more efficiently, especially in subterranean formations with a plurality of lithographies where the interface between two lithographies can create a section of the wellbore that is more susceptible to fracture and fluid loss. Accordingly, the present invention also provides for, in some embodiments, methods relating to the assessment of the WSM including methods that extend to the design of a wellbore strengthening fluid or additive thereof based on the assessment.

Greater or efficient wellbore strengthening may also provide for, in some embodiments, the capability to safely drill longer sections of a wellbore, which translates to less non-productive time and decreased costs. Further, longer drilled sections enable longer casing sections. Because each subsequent casing section is at a smaller diameter than the previous section, greater wellbore strengthening may ultimately allow for deeper wellbores and the capabilities to access previously untapped resources.

During drilling and other operations in an uncased wellbore, the wellbore can experience pressure surges as a result of, inter alia, initiating flow of a static or near static fluid and running drill pipe or casing. These pressure surges may briefly exceed fracture pressure of a portion of the subterranean formation and cause a point of fluid loss to form (e.g., a fracture or a microfracture). Strengthening a wellbore may mitigate induced points of fluid loss, which consequently mitigates the need for remedial treatments and nonproductive time.

Generally, after a section of the wellbore has been drilled, a casing is applied to the surface of the subterranean formation along the wellbore so as to prevent collapse of the wellbore, damage to the subterranean formation, fluid loss into the subterranean formation, and the like while additional wellbore sections are drilled. One method of casing a wellbore includes displacing the drilling fluid with a higher density fluid and then cementing. During the displacement of the drilling fluid, the uncased wellbore may be susceptible to damage, e.g., formation of a point of fluid loss, because the higher density fluid yields an overbalance pressure that is generally closer to the fracture pressure. Widening the mud weight window may advantageously mitigate and/or prevent the formation of a point of fluid loss during fluid displacement and casing operations.

Additionally, after a casing is set in a wellbore, the location in the wellbore that transitions from cased wellbore to uncased wellbore (e.g., the location of a casing shoe) may be one of the weakest points in the wellbore (i.e., the area with the greatest potential to fracture and cause fluid loss into the formation). In some operations, WSM is introduced into the wellbore first at higher concentration to create a "strong shoe" by strengthening the portion of the wellbore that transitions from cased to uncased. The present invention provides for, in some embodiments, developing wellbore strengthening fluids that may be capable of producing shoes with higher strengths and longer lifetimes. Enhanced shoes that strengthen wellbores at the transition from cased to uncased further provide for the benefits enumerated above, like the capability to safely drill longer sections of a wellbore.

It should be noted that when "about" is provided at the beginning of a numerical list, "about" modifies each number of the numerical list. It should be noted that in some numerical listings of ranges, some lower limits listed may be greater than some upper limits listed. One skilled in the art will recognize that the selected subset will require the selection of an upper limit in excess of the selected lower limit.

For simplicity, the term "test wellbore strengthening materials" (TWSM) as used herein refers to the WSM used in conjunction with measuring a property of a plug comprising the WSM with a tool of the present invention. Then, as used herein the term "designed wellbore strengthening materials" (DWSM) refers to the WSM used in wellbore strengthening fluids for use in wellbore operations based on the property of the plug comprising a TWSM (including any value derived therefrom, which are described in more detail below). It should be noted that the terms TWSM and DWSM should not be seen as limiting or exclusive compositions. That is, any WSM may be used as a TWSM or a DWSM.

Some embodiments may involve measuring a property of a plug comprising at least one TWSM using a Pore Plugging Apparatus, wherein the plug is lodged in a passageway of a tool of the present invention.

As used herein, the term "tool" refers to an implement that comprises at least one passageway extending from a first end through to an opposing end of the implement, where the passageway models an opening in a subterranean formation (e.g., a pore, a fracture, or a microfracture). As used herein, the term "Pore Plugging Apparatus" refers generally to an apparatus and/or system capable of applying differential pressures across passageway of a tool so as to form a plug in the passageway and/or apply differential pressures to a plug lodged in the passageway of the tool, and is described in more detail below.

A passageway is generally defined by an entry port, an exit port, and walls. In some embodiments, a passageway may be synthetic (e.g., machined or caused by applying pressure to a small opening formed in the tool), native (e.g., a natural fracture in a core sample), or a combination thereof (e.g., a natural fracture that was synthetically extended to have both an entry port and exit port).

In some embodiments, the entry and exit ports of a passageway may be substantially the same shape but sized differently. In some embodiments, a tool of the present invention may have a passageway with an entry port and an exit port with a shape of a slit (i.e., a substantially rectangular shape that is at least 50 times greater in length than width), an artificial or man-made fracture, or any hybrid thereof.

A suitable tool of the present invention may, in some embodiments, have a synthetic passageway with an entry port with the smallest dimension between about 1000 microns and about 6000 microns, an exit port with the smallest dimension between about 100 microns and about 3000 microns, and a length (i.e., the distance between the entry port and the exit port) between about 5 cm and 20 cm. One skilled in the art with the benefit of this disclosure should understand the size and shape of the synthetic passageway of a tool of the present invention may depend on, inter alia, the type of formation or formation microfractures where WSM may be employed in wellbore strengthening operations.

Figure 5:
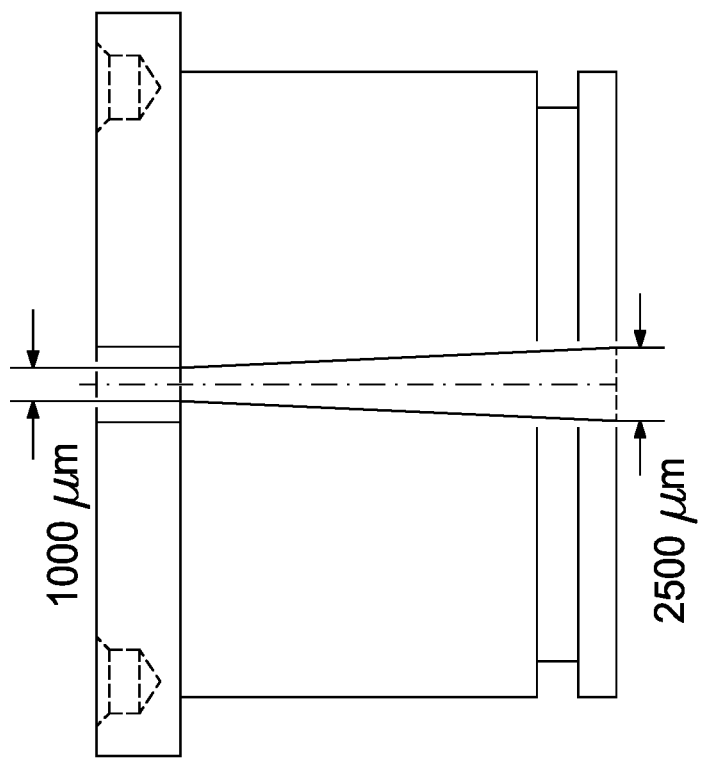
FIG. 5 provides a nonlimiting representation of a Tapered Cell, not necessarily to scale.
Figure 5:
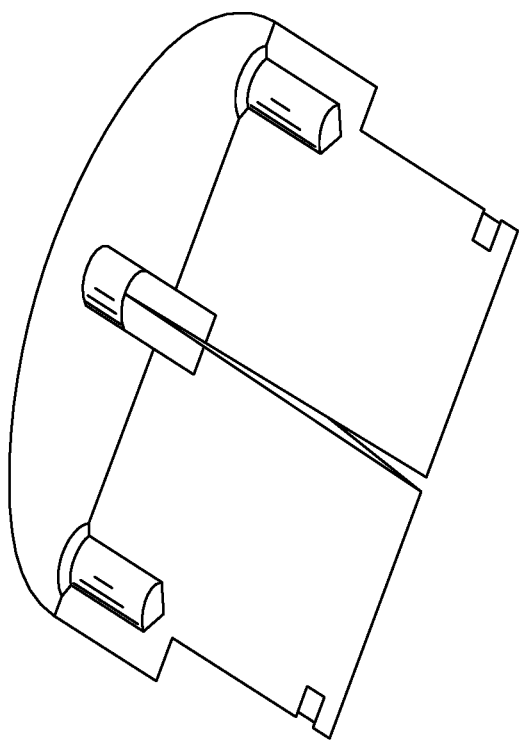

By way of nonlimiting example, a passageway may be a tapered slot. Generally, a tapered slot is a synthetic passageway with walls that taper from the size and shape of the entry port to the size and shape of the exit port. The tapering may be at a constant angle, at two or more angles with a sharp transition between angles, at two or more angles with a smooth transition between angles (e.g., rounded transitions), or any hybrid thereof. A nonlimiting example of a tool of the present invention having a tapered slot passageway is illustrated in FIG. 5 with an entry point 2500 microns across and exit point 1000 microns across.

In some embodiments, the walls (or at least one wall) of a passageway in a tool of the present invention may be adjustable so as to allow for changing the distance between opposing walls. Depending on the configuration of the adjustable walls, the entry port and/or exit port may also be adjustable so as to provide for adjustment of the smallest dimension of the entry port and/or exit port.

In some embodiments, a tool of the present invention may comprise a holder and insert capable of operably mating with a holder. A tool of the present invention comprising a holder and insert may advantageously allow for changing the dimensions of the passageway with greater ease and at less expense. Further, the incorporation of sensors in an insert, as described below, may advantageously provide for easier maintenance and care of the sensors including replacement of a sensor.

In some embodiments, measuring a property of a plug lodged in a passageway of a tool of the present invention may be achieved using at least one sensor coupled to the tool. A sensor coupled to a tool includes, but is not limited to, a sensor embedded in at least a portion of the tool, a sensor embedded in at least a portion of a tool component, a sensor disposed on at least a portion of the tool, a sensor disposed on at least a portion of a tool component, or any hybrid thereof.

Figure 6A:
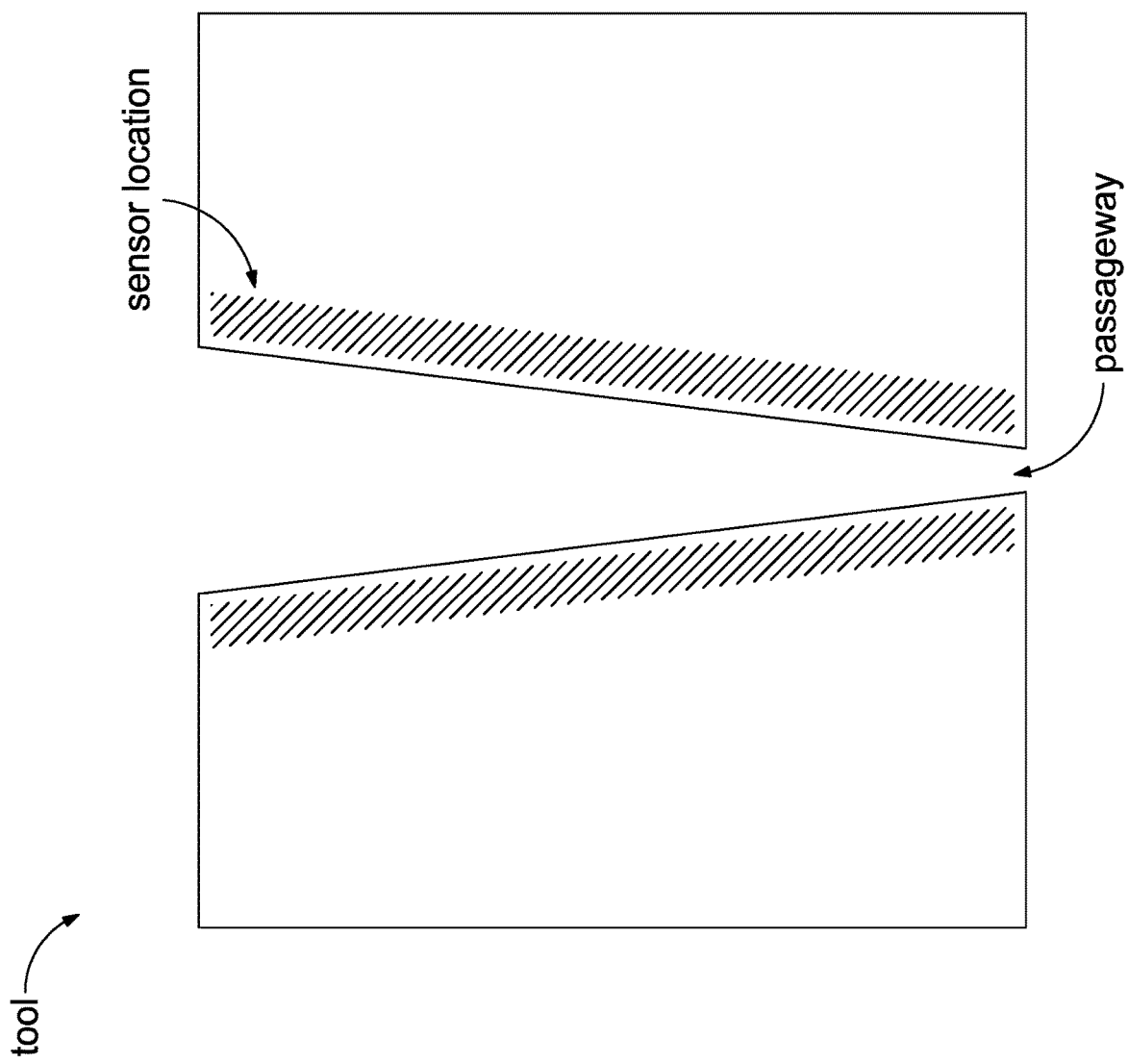
Figure 6C:
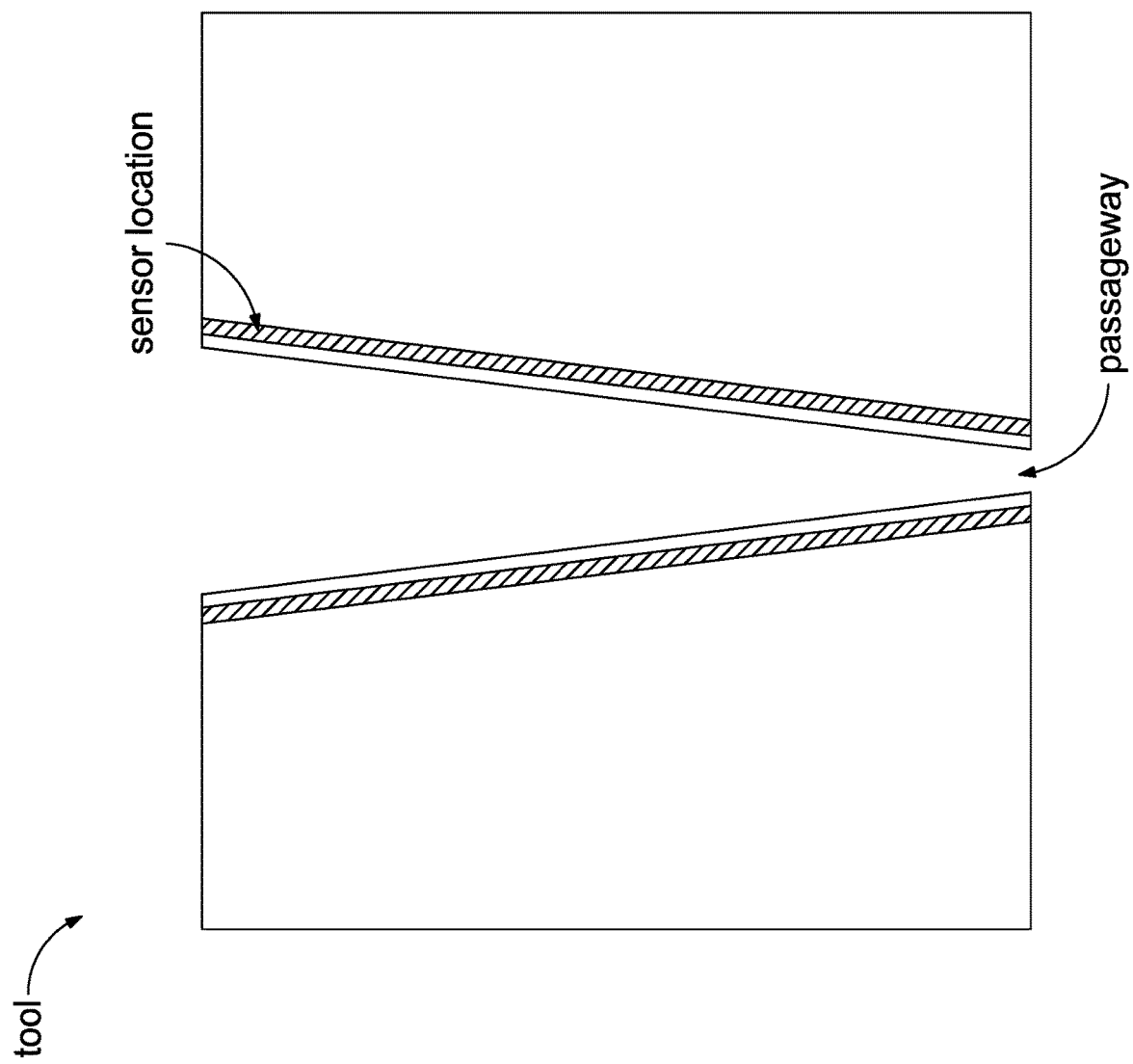
Figure 6D:
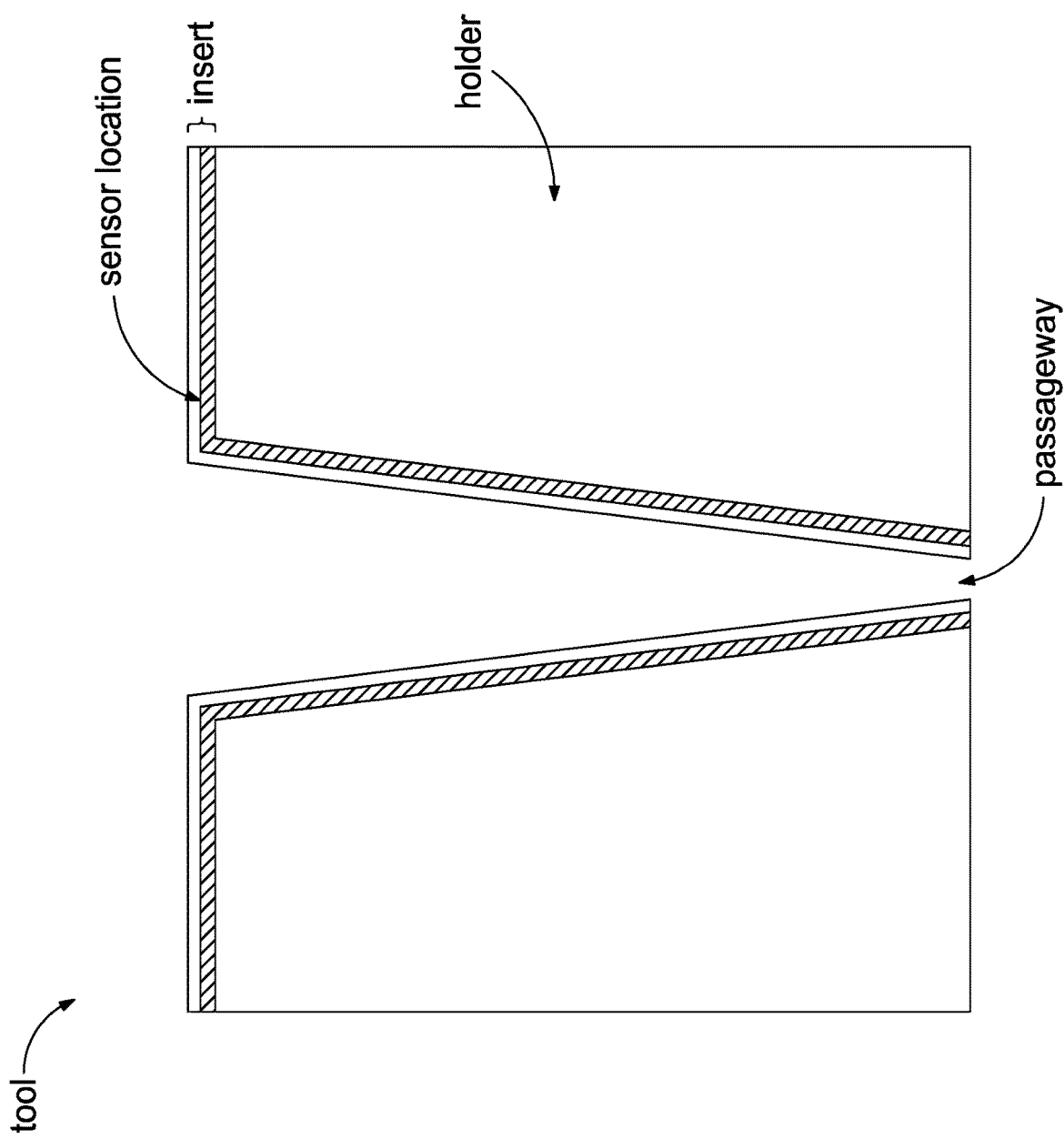

FIGS. 6A-E provide cross-sectional illustrations of non-limiting examples of tool/sensor configurations where hashmarks illustrate at least some of the locations a sensor may be coupled to a tool. FIG. 6A provides a tool cross-section illustrating that a sensor may be embedded in the tool proximal to the passageway of the tool. FIG. 6B provides a tool cross-section illustrating that a passageway wall may have a layer disposed thereon that the sensor is coupled to. FIG. 6C provides a tool cross-section illustrating that a passageway may have multiple layers were the sensor is coupled to a layer other than the layer proximal to the passageway. FIG. 6D provides a tool cross-section illustrating a tool comprising a holder and an insert, where the insert has more than one layer and the sensor may be coupled to a layer other than the layer proximal to the passageway. FIG. 6E provides a tool cross-section illustrating a tool comprising a holder and an insert, where the insert has more than one layer and the sensor may be coupled to a layer proximal to the passageway.

Suitable sensors for use in conjunction with a tool of the present invention may include, but are not limited to, force gauges, load cells, piezoelectric sensors, strain gauges, temperature gauges, temperature sensors, magnetic sensors, ultrasonic sensors and the like, or any hybrid thereof. Sensors for use in conjunction with a tool of the present invention may be in the form of sensor nodes, an array of sensor nodes, a wire sensor, a plate sensor, and the like, any hybrid thereof, or any combination thereof. Sensors for use in conjunction with a tool of the present invention may communicate with an output device (e.g., a computer, a display, and the like) through wires, wirelessly, or any combination thereof.

Figure 7A:
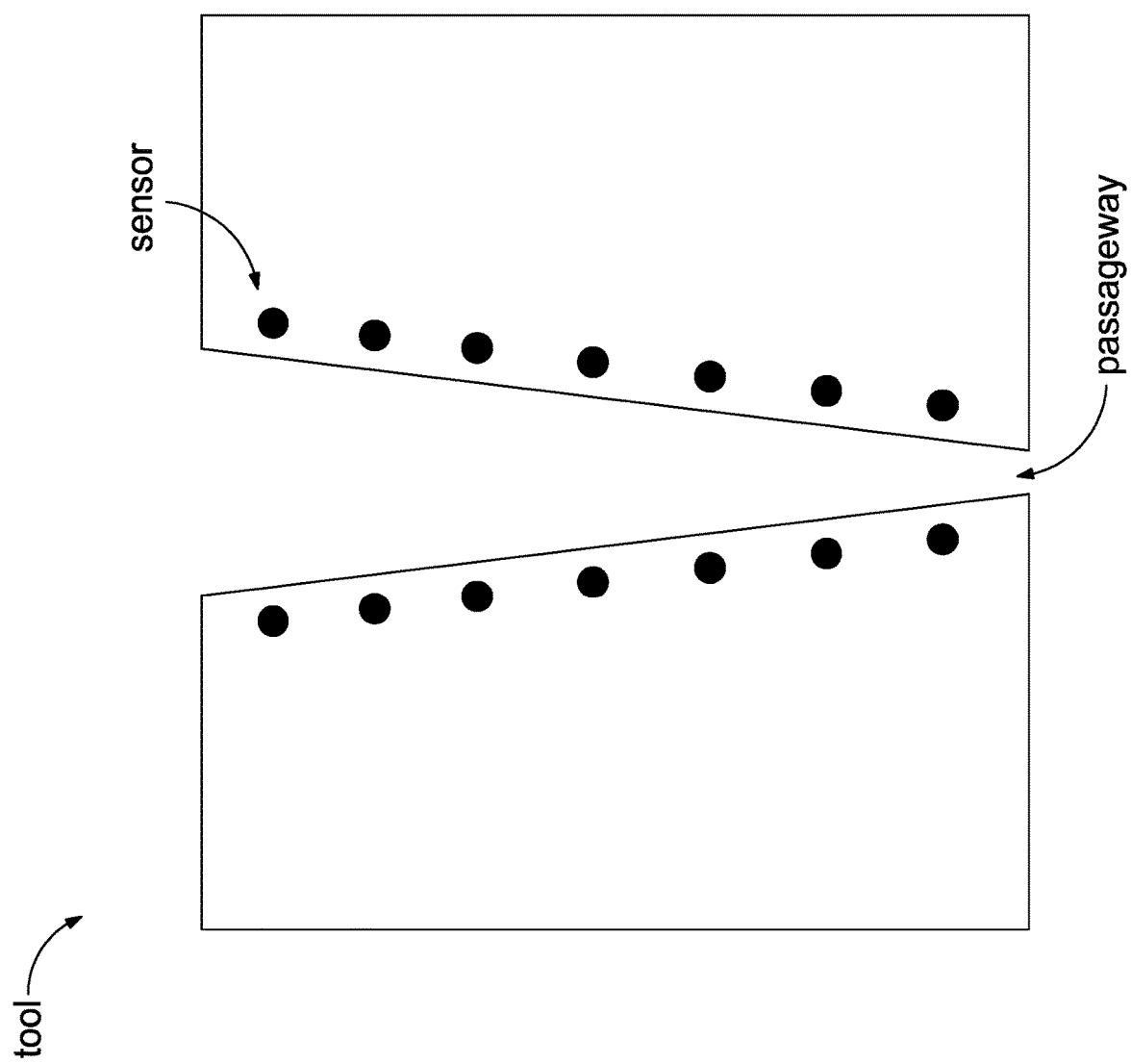
FIGS. 7A-B provide a cross-section and top view, respectively, of a tool having a plurality of node sensors embedded in the tool proximal to the passageway of the tool.
Figure 7B:
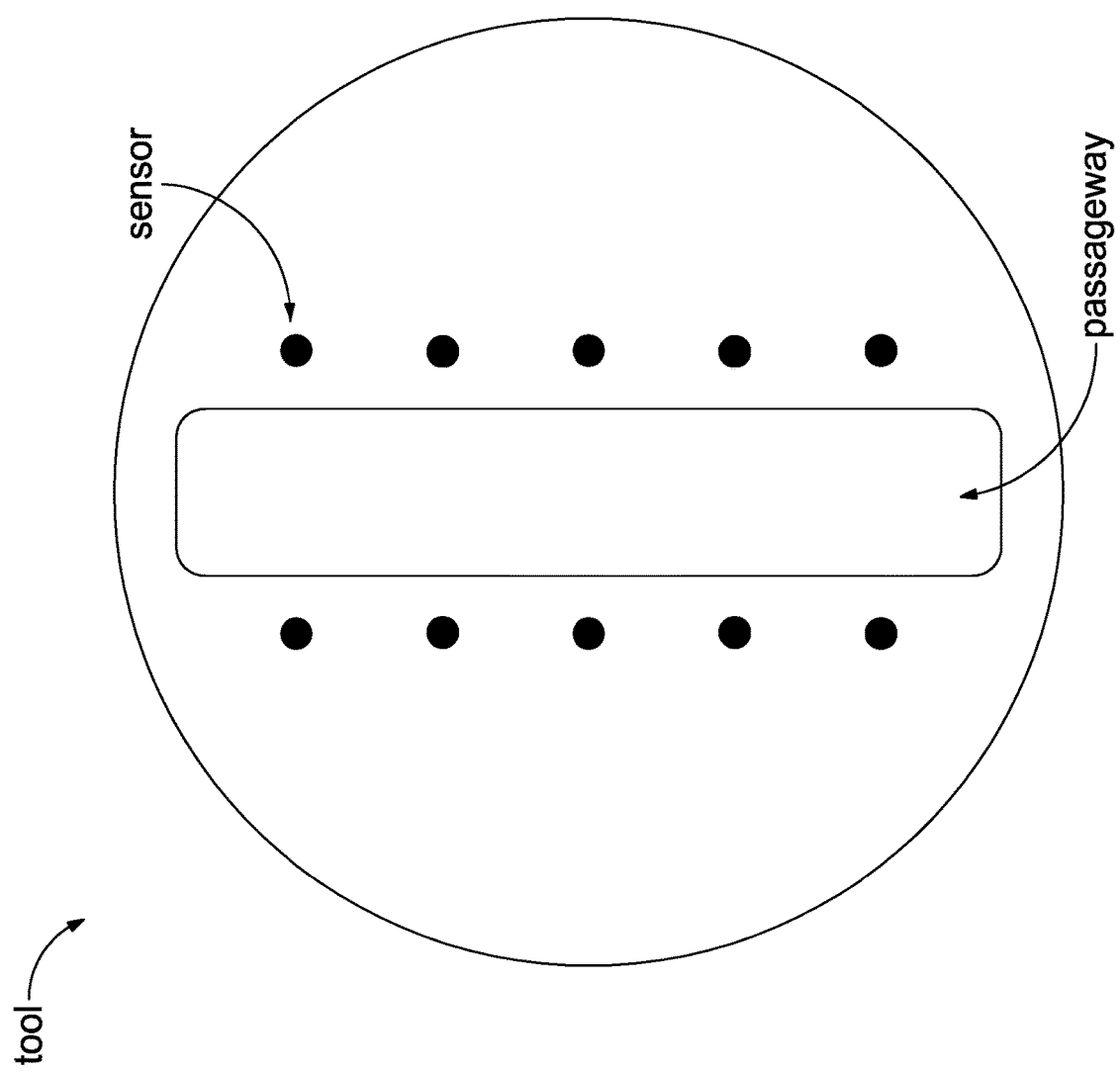
Figure 7C:
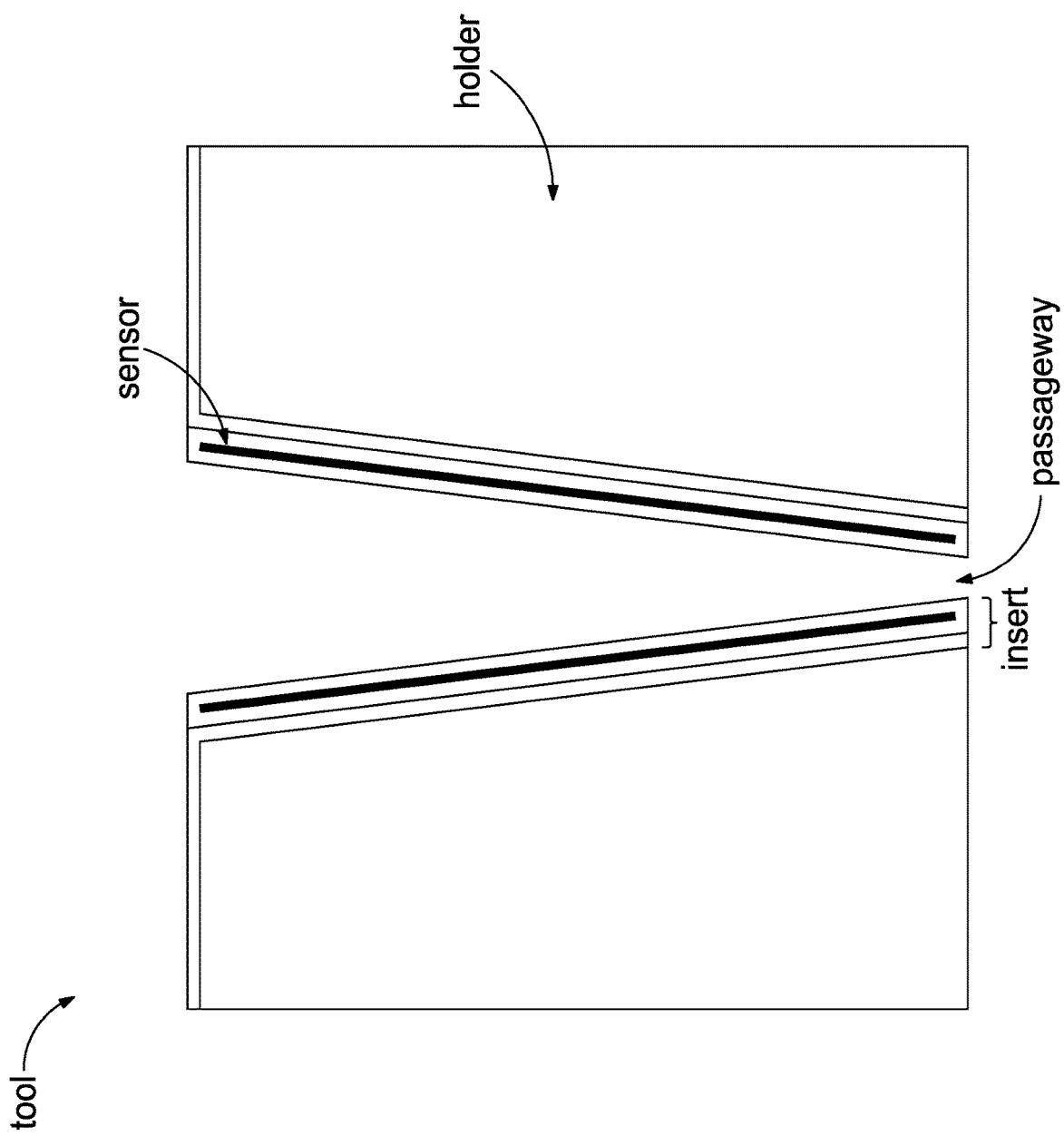
FIGS. 7C-D provide a cross-section and top view, respectively, of a tool comprising a holder and an insert, where the insert has two layers with a plurality of wire sensors embedded in the insert layer proximal to the passageway of the tool.
Figure 7D:
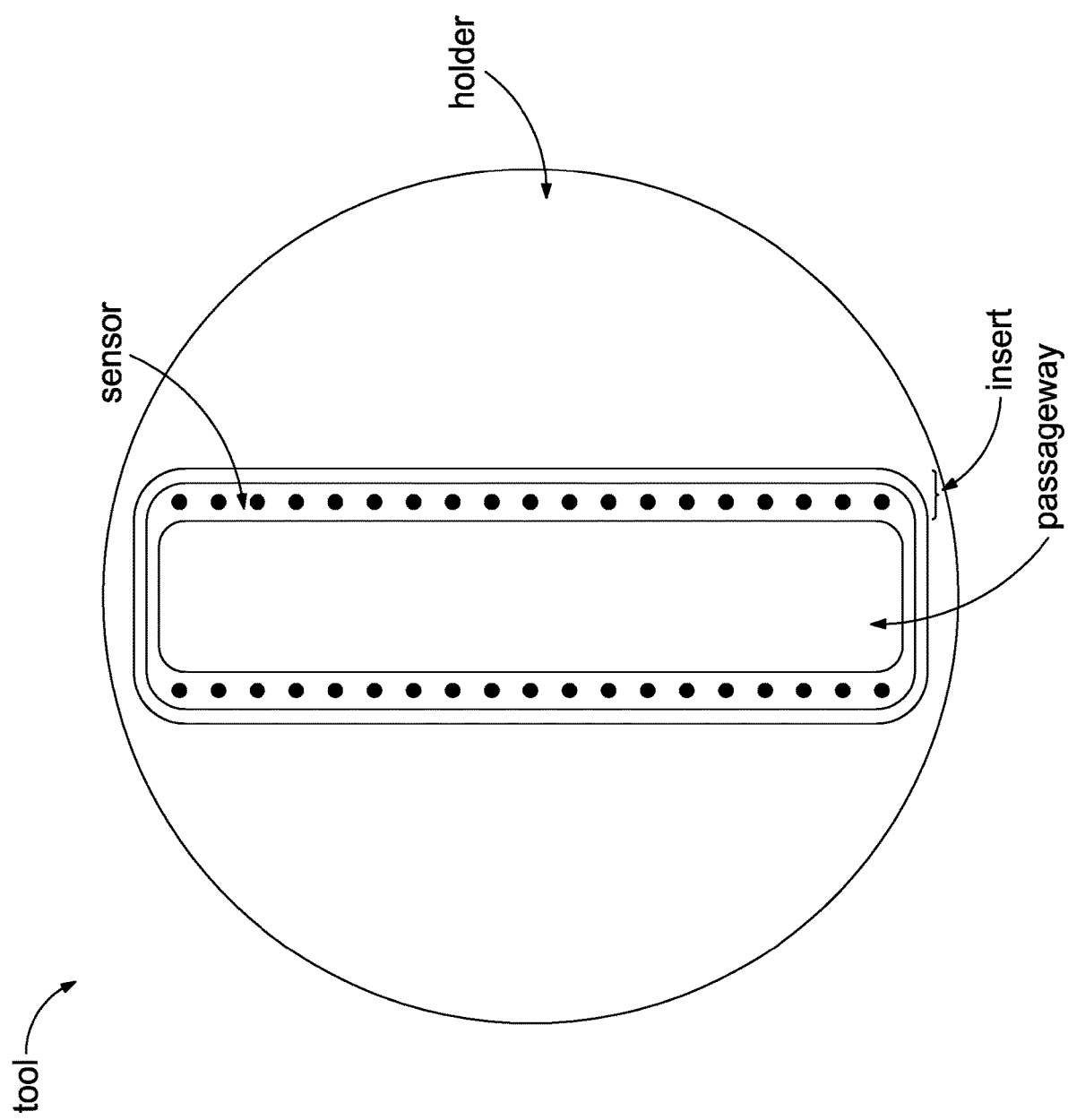

One skilled in the art, with the benefit of this disclosure, should understand the plurality of configurations that a tool of the present invention may comprise a sensor in a suitable location. By way of nonlimiting example, FIGS. 7A-B include a cross-section and top view, respectively, of a tool having a plurality of node sensors embedded in the tool proximal to the passageway of the tool, such that the plurality of sensors are arranged in a regular array along the height and width of the two long walls making up the passageway having an oblong cross-section. By way of another nonlimiting example, FIGS. 7C-D include a cross-section and top view, respectively, of a tool comprising a holder and an insert, where the insert has two layers with a plurality of wire sensors embedded in the insert layer proximal to the passageway of the tool.

Suitable plug properties that may be measured in a tool of the present invention may include, but are not limited to, a normal plug pressure and/or normal plug displacement. As used herein, the term "normal plug pressure" refers to the pressure exerted by a plug that is lodged in a passageway onto the walls of the passageway of the tool of the present invention. It should be noted that "normal plug pressure" is not limited to pressure exerted only at a 90° angle from the walls of the passageway, but rather is a more general term referring to pressure at any angle exerted from the plug onto the wall of the passageway. As used herein, the term "normal plug displacement" refers to the maximum distance a wall of a passageway of a tool of the present invention is displaced by a plug lodged in the passageway at a given pressure and/or differential pressure.

Figure 8B:
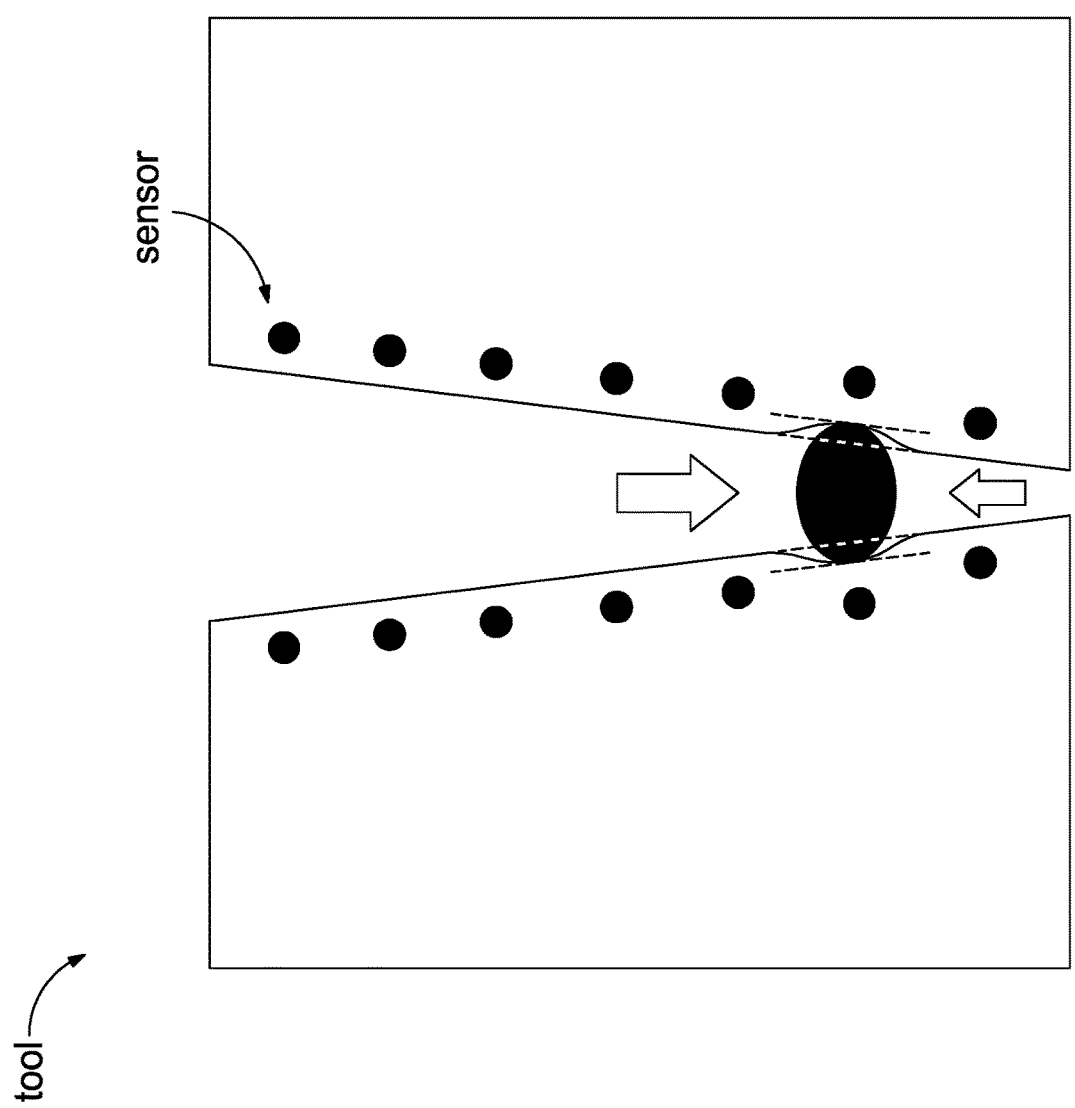
FIG. 8B provides a nonlimiting illustration of a plug exerting a normal plug displacement on a passageway of a tool having sensors.

Some embodiments may involve measuring a normal plug pressure and/or normal plug displacement at a plurality of differential pressures exerted on the plug in the passageway direction. FIG. 8A provides a nonlimiting illustration of a plug lodged in a passageway of a tool having sensors, where the sensors are capable of measuring the normal plug pressure at a given differential pressure exerted in the passageway direction, where the pressure towards the exit port of the passageway is greater than the pressure towards the entry port of the passageway. FIG. 8B provides a nonlimiting illustration of a plug lodged in a passageway of a tool having sensors, where the sensors are capable of measuring the normal plug displacement at a given differential pressure exerted in the passageway direction, where the pressure towards the exit port of the passageway is greater than the pressure towards the entry port of the passageway.

Suitable materials that a tool of the present invention, or portion thereof (e.g., a portion of an insert, a holder, or a coating) may be formed of may include, but are not limited to, metal (e.g., stainless steel), cork, synthetic cork, a core sample, synthetic core, sandstone, ceramic, resin, polymers, polymer composites, epoxy, or any combination thereof. Because sensors used in conjunction with the present invention generally measure forces exerted on a wall of a passageway of a tool, the material between the sensor and the surface of the wall may, in some embodiments, advantageously be deformable, reversibly or irreversibly. Suitable deformable materials may include, but are not limited to, cork, synthetic cork, resins, polymers, polymer composites, epoxies, or any combination thereof.

In some embodiments, the material that forms a tool of the present invention, or portion thereof, may have a permeability ranging from a lower limit of impermeable, 1 nD, 10 nD, 25 nD, 50 nD, 100 nD, or 500 nD to an upper limit of about 10 milliDarcy (mD), 1 mD, 500 microD, 100 microD, 10 microD, or 500 nD, and wherein the permeability may range from any lower limit to any upper limit and encompass any subset therebetween. By way of nonlimiting example, a stainless steel tool may be impermeable, while a tool made of sandstone may have a permeability of about 10 mD. One skilled in the art with the benefit of this disclosure should understand the choice of a permeability of the material that forms a tool may depend on, inter alia, the type of formation or formation microfractures where WSM may be employed in wellbore strengthening operations.

Generally, methods of the present invention include, in some embodiments, forming a plug of TWSM in a tool of the present invention and then applying a pressure or differential pressure to the plug while measuring a normal plug pressure and/or a normal plug displacement of the plug of TWSM. In some embodiments, measuring a normal plug pressure and/or a normal plug displacement may occur during formation of the plug.

Figure 9:
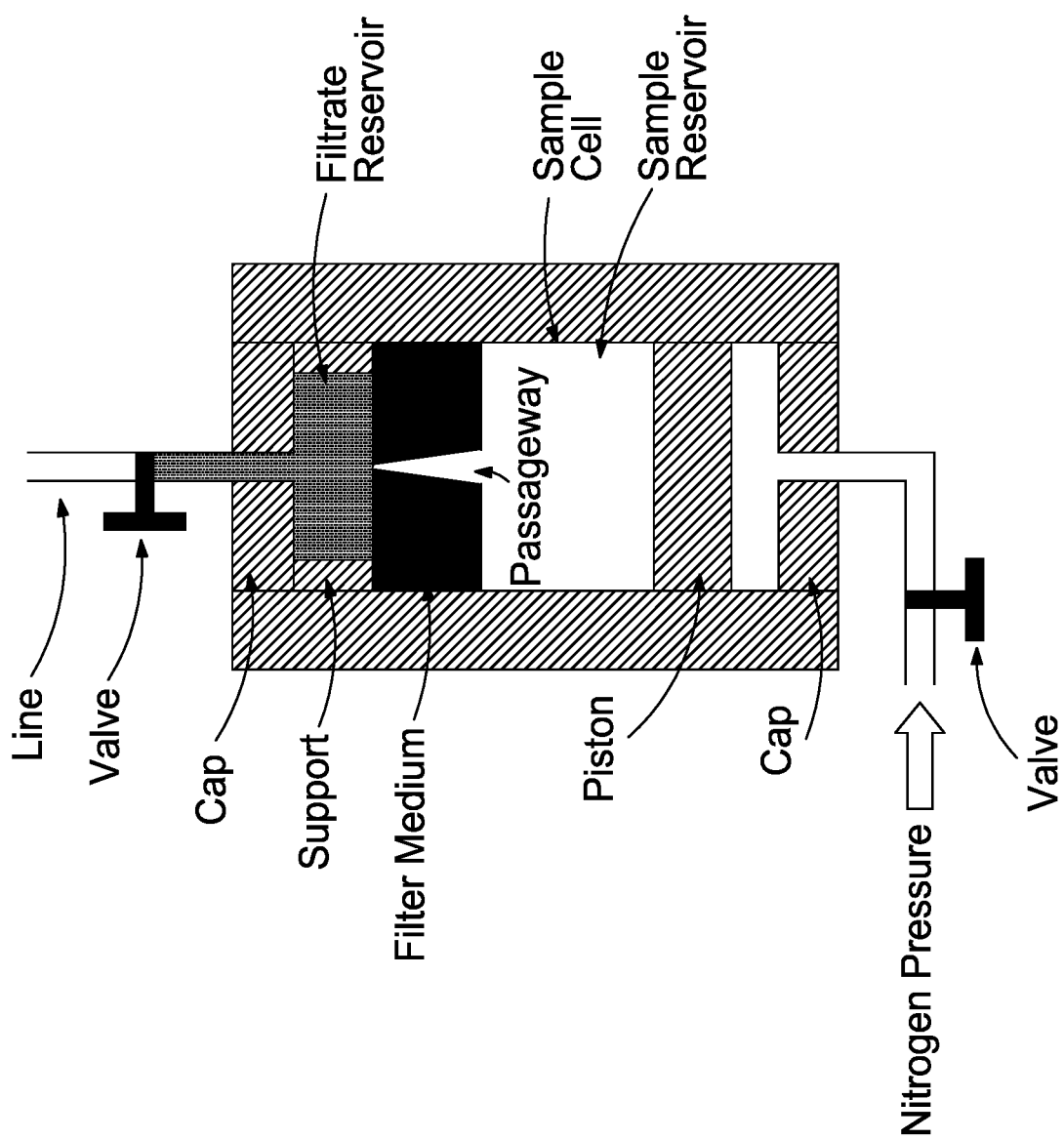
FIG. 9 provides a nonlimiting representation of a Pore Plugging Apparatus, not necessarily to scale.

By way of nonlimiting example, forming a plug may involve a Pore Plugging Apparatus, a nonlimiting example of which is illustrated in FIG. 9, comprising in series a 500-mL volume sample cell having a movable piston, a tool having a passageway therethrough with sensor along the passageway, and an assembly for collecting the filtrate while testing (illustrated as supports, a filtrate reservoir, a cap, and valve in FIG. 9). As shown in FIG. 9, the sample cell is positioned such that pressure may be applied from the bottom so as to push the sample in the sample reservoir through the passageway and collect the filtrate in the filtrate reservoir above. This inverted configuration may help prevent components of the wellbore strengthening fluid that settle during the static test from contributing to the performance of the TWSM. Forming a plug in a Pore Plugging Apparatus may generally be achieved by passing a fluid comprising a TWSM of interest through an appropriate tool at increasing differential pressures until a plug is formed, i.e., no whole fluid (e.g., the mud including fluids and solids) is able to pass through the tool.

Once a plug of TWSM is formed in a tool of the present invention, some embodiments of the present invention may involve applying pressure or differential pressure to the plug of TWSM in the Pore Plugging Apparatus; and measuring a normal plug pressure and/or normal plug displacement of the plug of TWSM. In some embodiments, applying pressure to the plug of TWSM may be done in the same Pore Plugging Apparatus or a different Pore Plugging Apparatus. Further, in some embodiments, applying pressure to the plug of TWSM may be done with a fluid other than the wellbore strengthening fluid, e.g., a drilling fluid or the base fluid of a drilling fluid. Using another fluid, especially a fluid not comprising a TWSM, may advantageously provide for a better analysis of the wellbore strengthening properties of the plug.

By way of nonlimiting example, after the plug is formed in the tool, a Pore Plugging Apparatus may be loaded with a drilling fluid that does not contain TWSM. Pressure may be applied from the bottom, as described above, in 100 psi intervals as illustrated in FIG. 9. At each interval, a normal plug pressure and/or normal plug displacement of the plug may be measured. Alternatively, a normal plug pressure and/or normal plug displacement of the plug may be measured continuously, i.e., during pressure increases and pressure sustaining. As shown in FIG. 9, the pressure or differential pressure continues through the plug break pressure, i.e., the pressure at which the plug allows whole drilling fluid to pass through the tapered slot. It should be noted that as described in this example, the Plug Pressure Test involves testing the tool in the Pore Plugging Apparatus in which the plug was formed. However, in some embodiments, the tool may be transferred to a second Pore Plugging Apparatus for testing after the plug is formed.

Figure 10A:
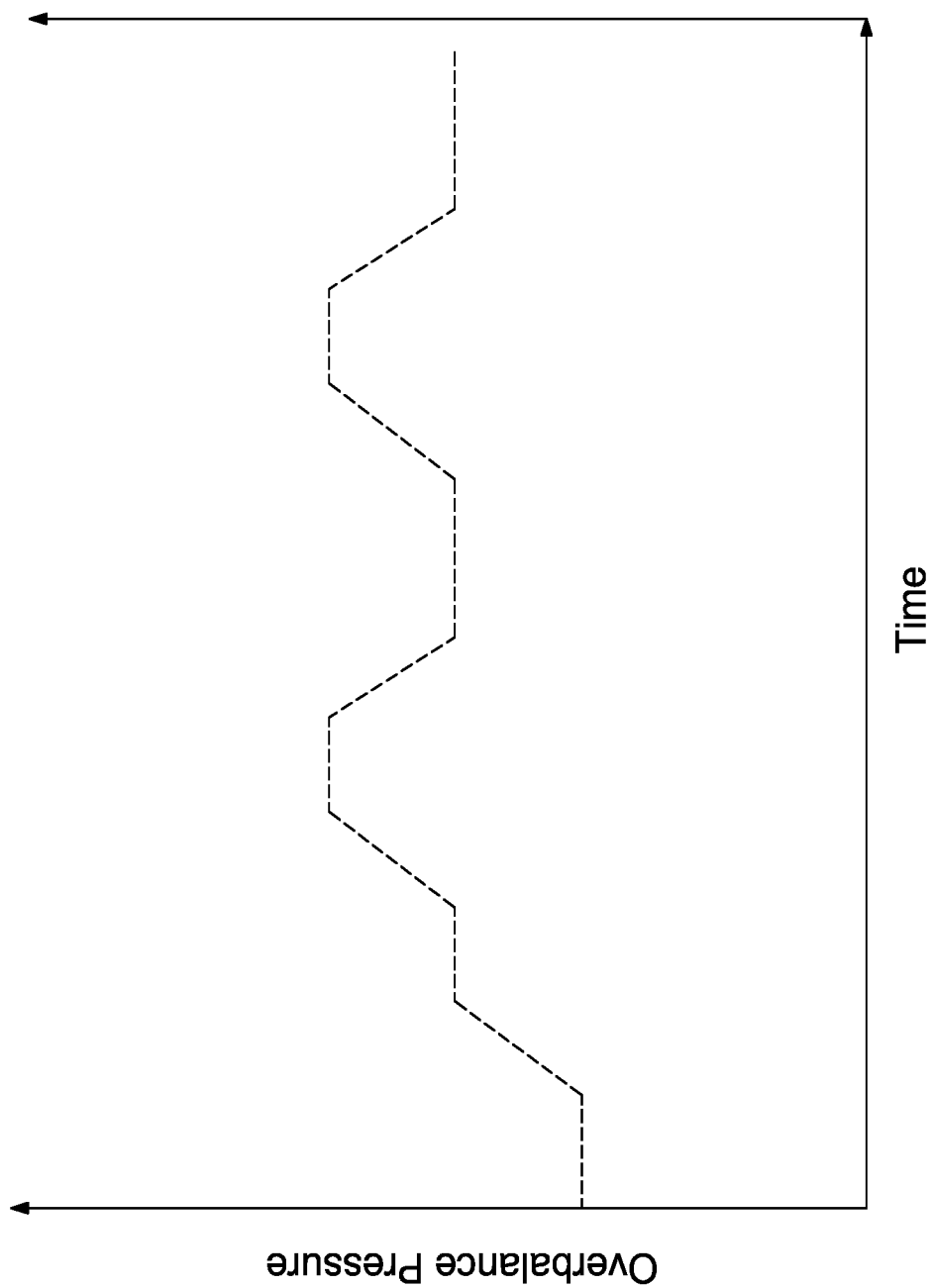
FIGS. 10A-C provide illustrations of suitable pressure application procedures that may be applied to a plug while measuring a normal plug pressure and/or normal plug displacement of the plug.
Figure 10B:
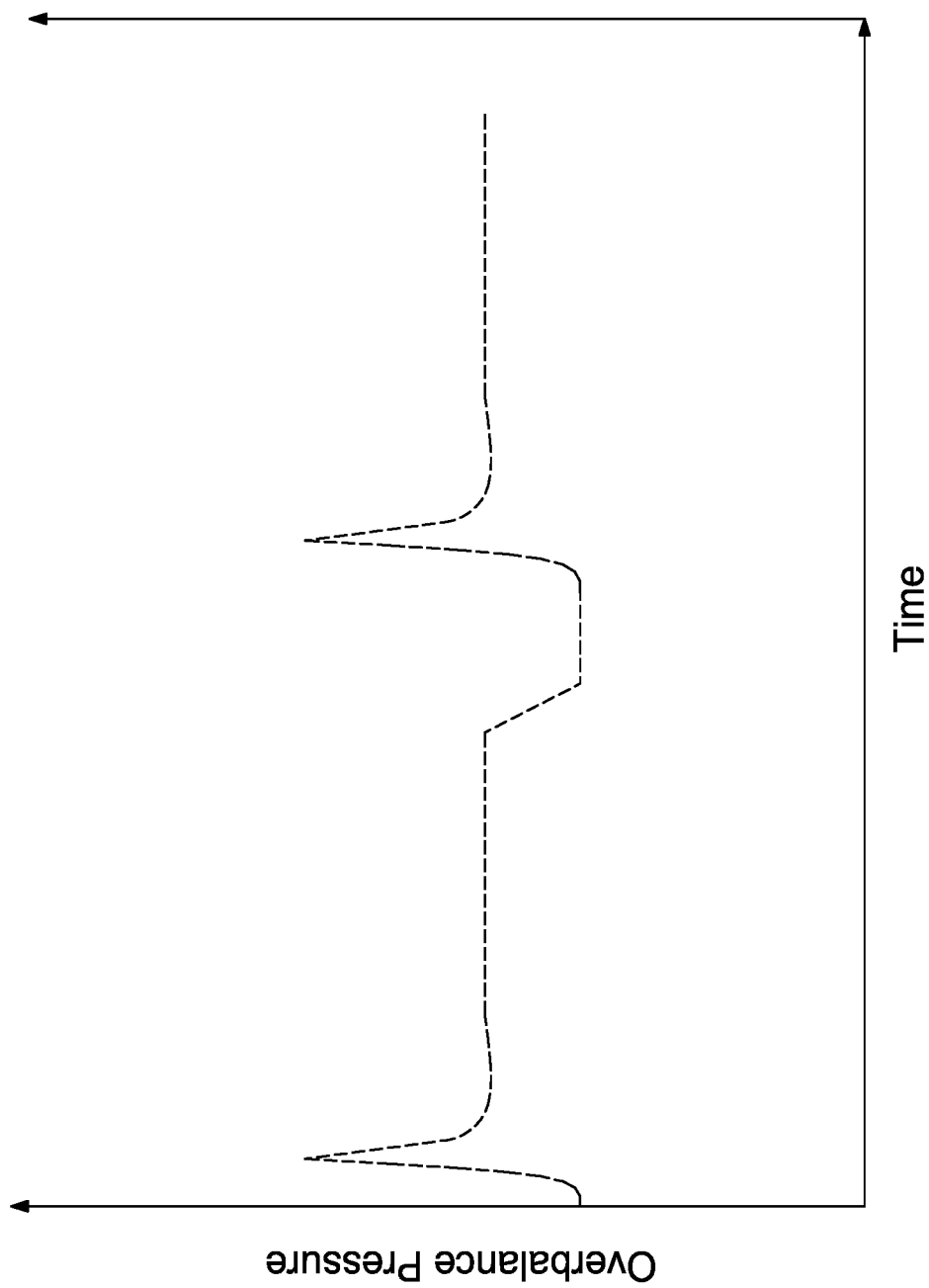
Figure 10C:
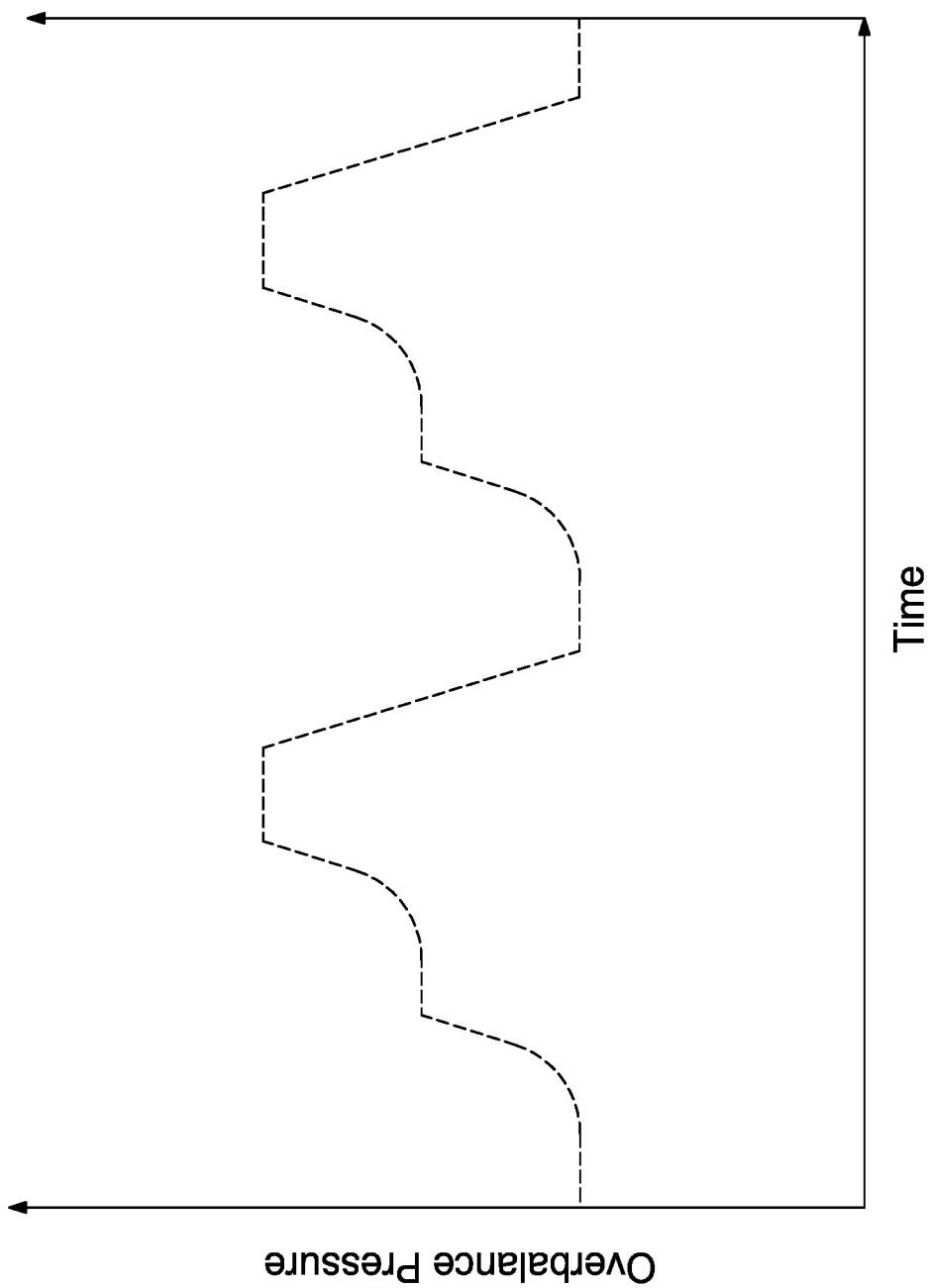

One skilled in the art with the benefit of this disclosure should understand the plurality suitable pressure application procedures for applying pressure or differential pressure to the plug while measuring a normal plug pressure and/or normal plug displacement of the plug. Examples of suitable pressure application procedures may include, but are not limited to, a steady increase in pressure or differential pressure, an exponential increase in pressure or differential pressure, a step-wise increase in pressure or differential pressure, a steady decrease in pressure or differential pressure, an exponential decrease in pressure or differential pressure, a step-wise decrease in pressure or differential pressure, any hybrid thereof, or any combination thereof. By way of nonlimiting example, FIGS. 10A-C provide illustrations of suitable pressure application procedures that may be applied to a plug while measuring a normal plug pressure and/or normal plug displacement of the plug. FIG. 10A illustrates a pressure application procedure including, in order, a steady pressure at the initial overburden pressure (equal to the fracture pressure), a steady increase and then sustained pressure, a steady increase and then sustained pressure, a steady decrease and then sustained pressure, a steady increase and then sustained pressure, and finally a steady decrease and then sustained pressure greater than the initial overburden pressure. FIG. 10B illustrates a pressure application procedure including, in order, starting from the initial overburden pressure (equal to the fracture pressure) an exponential increase and then exponential decrease to a sustained pressure greater than the pore forming pressure, a steady decrease and then sustained pressure at the pore forming pressure, and finally an exponential increase and then exponential decrease to a sustained pressure greater than the overburden pressure. This pressure application procedure, and others like it, may advantageously simulate pressure spikes that may be experienced in a wellbore when, for example, pumps are turned on. FIG. 10C illustrates a pressure application procedure including, in order, starting from the initial overburden pressure (equal to the fracture pressure) a brief sustained pressure followed by an exponential increase in pressure, another sustained pressure then an exponential increase in pressure followed by a more prolonged sustained pressure, then a steady state decrease in pressure, and then a repeat of the pressure application procedure. Repetition within a pressure application procedure may advantageously provide insight into the durability of a plug comprising TWSM.

Some embodiments of the present invention may involve forming a plug of TWSM in a Pore Plugging Apparatus; applying pressure or differential pressure to the plug of TWSM in the Pore Plugging Apparatus; and measuring a normal plug pressure and/or normal plug displacement of the plug of TWSM. Some embodiments of the present invention may involve forming a plug of TWSM in a Pore Plugging Apparatus; applying a series of pressures or differential pressures to the plug of TWSM in the Pore Plugging Apparatus; and measuring a normal plug pressure and/or normal plug displacement of the plug of TWSM for at least one of the pressures or differential pressures in the series.

In some embodiments, a normal plug pressure and/or normal plug displacement of a plug may be used to calculate a plurality of values applicable to wellbore strengthening, e.g., sustained increased hoop stress, compressive strength of the plug, shear strength of the plug, and any combination thereof. By way of nonlimiting example, a characteristic of the plug may be used to calculate the range of wellbore hoop stresses in which a plug of a given WSM composition is operable. For example, the normal plug pressure may be directly proportional to near wellbore hoop stress, i.e., increase in the normal plug pressure may translate to increase in the near wellbore hoop stress. Further, the compressive strength of the plug may also be proportional to the normal plug pressure and/or normal plug displacement.

In some embodiments, a normal plug pressure, normal plug displacement, and/or values applicable to wellbore strengthening may be used, at least in part, to determine a relative wellbore strengthening capability for a given TWSM. As used herein, "relativity," as it relates to wellbore strengthening capability, refers both to the relative comparison between two or more TWSM and the comparison of one or more TWSM to a wellbore strengthening scale. Because a normal plug pressure, normal plug displacement, and/or values applicable to wellbore strengthening, and consequently the relative wellbore strengthening values, depend on, inter alia, the configuration of the passageway and the tool material, a wellbore strengthening capability scale may be dependent on, inter alia, the configuration of the passageway and the material(s) from which the tool or component thereof is made.

Some embodiments of the present invention may involve determining a relative wellbore strengthening value of a TWSM based on, at least in part, a normal plug pressure, normal plug displacement, and/or values applicable to wellbore strengthening. Further, if measurements of a normal plug pressure and/or normal plug displacement are performed at a plurality of pressures and/or differential pressures, then the plurality of normal plug pressure, normal plug displacement, and/or values applicable to wellbore strengthening may be used to determine a relative wellbore strengthening value of a TWSM.

Generally, a normal plug pressure, normal plug displacement, and/or values applicable to wellbore strengthening of a plug of TWSM and/or a relative wellbore strengthening capability of a TWSM may be used to design wellbore strengthening fluids and/or wellbore strengthening additives.

In some embodiments, wellbore strengthening fluids and/or wellbore strengthening additives may comprise DWSM that are the same or different than the TWSM. The similarities or differences may be in the composition, the concentration, the relative concentration when two or more WSM are employed, the size distribution, and the like, or any combination thereof. By way of nonlimiting example, TWSM may include carbon fibers with an aspect ratio of about 15 in combination with silica particles with an average diameter of about 250 microns, while the DWSM of a designed wellbore strengthening additive may include carbon fibers with an aspect ratio of about 15 in combination with silica particles with an average diameter of about 500 microns. By way of another nonlimiting example, a series of TWSM may include rayon fibers with differing relative concentrations of resilient graphitic carbon and ground walnut shells, while the DWSM of a designed wellbore strengthening fluid may include rayon fibers with resilient graphitic carbon and ground walnut shells in a relative concentration not tested.

Some embodiments may involve introducing a wellbore strengthening fluid (or a wellbore strengthening additive) into at least a portion of a wellbore penetrating a subterranean formation, where the wellbore strengthening fluid (or wellbore strengthening additive) comprises DWSM. Some embodiments may involve introducing a wellbore strengthening fluid (or a wellbore strengthening additive) comprising a DWSM into a portion of a wellbore penetrating a subterranean formation so as to produce a strengthened wellbore section.

Some embodiments may involve strengthening at least a portion of a wellbore during a drilling operation, i.e., while drilling at least a portion of a wellbore penetrating a subterranean formation. In some embodiments, a drilling fluid may comprise a base fluid and DWSM. In some embodiments, a drilling fluid may comprise a base fluid and a designed wellbore strengthening additive. Suitable base fluids for drilling fluids include suitable base fluids for wellbore strengthening fluid and are provided further herein.

Some embodiments may involve drilling a wellbore before, after, and/or during the strengthening of the wellbore. In some embodiments, a drilling fluid not comprising a DWSM may be used before or after a wellbore strengthening fluid (or wellbore strengthening additive) comprising a DWSM. In such embodiments, fluids consecutively introduced into the wellbore may have the same or different compositions and/or the same or different characteristics, e.g., density and/or weight. Some embodiments may involve substantially removing, e.g., flushing, a fluid (or additive) from the wellbore before introduction of the subsequent fluid. Some embodiments may involve changing the fluid on-the-fly so as to provide for wellbore strengthening with DWSM as needed.

In some embodiments, a drilling fluid used after strengthening a wellbore with DWSM may have an increased equivalent circulating density relative to a drilling fluid used before strengthening the wellbore. Equivalent circulating density, as used herein, refers to the effective density exerted by a circulating fluid against a formation that takes into account the pressure drop in the annulus about the point being considered. Equivalent circulating density may be affected by various parameters including, but not limited to, the viscosity of the drilling fluid, the pump rate, the drilling fluid weight, the annulus size, and any combination thereof. Wellbore strengthening increases the near-wellbore stresses, e.g., circumferential stresses, which may allow for a higher mud weight window to be sustained.

In some embodiments, a drilling fluid used after strengthening a wellbore with DWSM may have an increased drilling fluid weight relative to a drilling fluid used before strengthening the wellbore. In some embodiments, the drilling fluid weight may range from drilling fluid weights corresponding to about the pore pressure to drilling fluid weights corresponding to about the fracture pressure. In some embodiments, the drilling fluid weights corresponding to pore pressure may range from about 2 ppg (pounds per gallon) to about 20 ppg. The drilling fluid weights corresponding to fracture pressure can be determined with a leak off test, which is commonly known to one skilled in the art, when performed to determine the maximum pressure a formation can sustain.

Wellbore Strengthening Materials and Wellbore Strengthening Fluids

Suitable WSM for use in conjunction with the present invention may include, but are not limited to, particulates, fibers, and any combination thereof. The particulate and/or fiber may be natural or synthetic, degradable or nondegradable, and mixtures thereof. It should be understood that the term "particulate" or "particle," as used herein, includes all known shapes of materials, including substantially spherical materials, crenulated materials, low aspect ratio materials, polygonal materials (such as cubic materials), discus, hybrids thereof, and any combination thereof. It should be understood that the term "fiber," as used herein, includes all known shapes of materials with medium to high aspect ratios, including filaments and collections of filaments. In some embodiments, the aspect ratio of a fiber may range from a lower limit of about 5, 10, or 25 to an unlimited upper limit. While the aspect ratio upper limit is believed to be unlimited, the aspect ratio of applicable fibers may range from a lower limit of about 5, 10, or 25 to an upper limit of about 10,000, 5000, 1000, 500, or 100, and wherein the aspect ratio may range from any lower limit to any upper limit and encompass any subset therebetween. In some embodiments, the length of a fiber may range from a lower limit of about 150, 250, 500, or 1000 microns to an upper limit of about 6000, 5000, 2500, or 1000, and wherein the fiber length may range from any lower limit to any upper limit and encompass any subset therebetween. Fibers may be swellable, i.e., increase in volume by absorbing solvent. Fibers may be aggregates of filaments where the aggregate may or may not have a medium to high aspect ratio.

In some embodiments, at least one particulate may be used in combination with at least one fiber in a wellbore strengthening fluid. Suitable particulates and/or fiber may include those comprising materials suitable for use in a subterranean formation including, but not limited to, any known lost circulation material, bridging agent, fluid loss control agent, diverting agent, plugging agent, and the like, and any combination thereof. Examples of suitable materials may include, but not be limited to, sand, shale, ground marble, bauxite, ceramic materials, glass materials, metal pellets, high strength synthetic fibers, resilient graphitic carbon, cellulose flakes, wood, resins, polymer materials (crosslinked or otherwise), polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, composite materials, and any combination thereof. Suitable composite materials may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and any combination thereof.

In some embodiments, particulates and/or fibers may comprise a degradable material. Nonlimiting examples of suitable degradable materials that may be used in the present invention include, but are not limited to, degradable polymers (crosslinked or otherwise), dehydrated compounds, and/or mixtures of the two. In choosing the appropriate degradable material, one should consider the degradation products that will result. As for degradable polymers, a polymer is considered to be "degradable" herein if the degradation is due to, inter alia, chemical and/or radical process such as hydrolysis, oxidation, enzymatic degradation, or UV radiation. Polymers may be homopolymers, random, linear, crosslinked, block, graft, and star- and hyper-branched. Such suitable polymers may be prepared by polycondensation reactions, ring-opening polymerizations, free radical polymerizations, anionic polymerizations, carbocationic polymerizations, and coordinative ring-opening polymerization, and any other suitable process. Specific examples of suitable polymers include polysaccharides such as dextran or cellulose; chitin; chitosan; proteins; orthoesters; aliphatic polyesters; poly(lactide); poly(glycolide); poly(ε-caprolactone); poly(hydroxybutyrate); poly(anhydrides); aliphatic polycarbonates; poly(orthoethers); poly(amino acids); poly(ethylene oxide); polyphosphazenes; and any combination thereof. Of these suitable polymers, aliphatic polyesters and polyanhydrides are preferred. Dehydrated compounds may be used in accordance with the present invention as a degradable solid particulate. A dehydrated compound is suitable for use in the present invention if it will degrade over time as it is rehydrated. For example, particulate solid anhydrous borate material that degrades over time may be suitable. Specific examples of particulate solid anhydrous borate materials that may be used include, but are not limited to, anhydrous sodium tetraborate (also known as anhydrous borax) and anhydrous boric acid. Degradable materials may also be combined or blended. One example of a suitable blend of materials is a mixture of poly(lactic acid) and sodium borate where the mixing of an acid and base could result in a neutral solution where this is desirable. Another example would include a blend of poly(lactic acid) and boric oxide, a blend of calcium carbonate and poly(lactic) acid, a blend of magnesium oxide and poly(lactic) acid, and the like. In certain preferred embodiments, the degradable material is calcium carbonate plus poly(lactic) acid. Where a mixture including poly(lactic)

acid is used, in certain preferred embodiments the poly (lactic) acid is present in the mixture in a stoichiometric amount, e.g., where a mixture of calcium carbonate and poly(lactic) acid is used, the mixture comprises two poly (lactic) acid units for each calcium carbonate unit. Other blends that undergo an irreversible degradation may also be suitable, if the products of the degradation do not undesirably interfere with either the conductivity of the filter cake or with the production of any of the fluids from the subterranean formation.

Specific examples of suitable particulates may include, but not be limited to, BARACARB® particulates (ground marble, available from Halliburton Energy Services, Inc.) including BARACARB® 5, BARACARB® 25, BARACARB® 150, BARACARB® 600, BARACARB® 1200; STEELSEAL® particulates (resilient graphitic carbon, available from Halliburton Energy Services, Inc.) including STEELSEAL® powder, STEELSEAL® 50, STEELSEAL® 150, STEELSEAL® 400 and STEELSEAL® 1000; WALL-NUT® particulates (ground walnut shells, available from Halliburton Energy Services, Inc.) including WALL-NUT® M, WALL-NUT® coarse, WALL-NUT® medium, and WALL-NUT® fine; BARAPLUG® (sized salt water, available from Halliburton Energy Services, Inc.) including BARAPLUG® 20, BARAPLUG® 50, and BARAPLUG® 3/300; BARAFLAKE® (calcium carbonate and polymers, available from Halliburton Energy Services, Inc.); and the like; and any combination thereof.

Further examples of suitable fibers may include, but not be limited to, fibers of cellulose including viscose cellulosic fibers, oil coated cellulosic fibers, and fibers derived from a plant product like paper fibers; carbon including carbon fibers; melt-processed inorganic fibers including basalt fibers, woolastonite fibers, non-amorphous metallic fibers, metal oxide fibers, mixed metal oxide fibers, ceramic fibers, and glass fibers; polymeric fibers including polypropylene fibers and poly(acrylic nitrile) fibers; metal oxide fibers; mixed metal oxide fibers; and the like; and any combination thereof. Examples may also include, but not be limited to, PAN fibers, i.e., carbon fibers derived from poly(acrylonitrile); PANEX® fibers (carbon fibers, available from Zoltek) including PANEX® 32, PANEX® 35-0.125", and PANEX® 35-0.25"; PANOX® (oxidized PAN fibers, available from SGL Group); rayon fibers including BDF™ 456 (rayon fibers, available from Halliburton Energy Services, Inc.); poly(lactide) ("PLA") fibers; alumina fibers; cellulosic fibers; BAROFIBRE® fibers including BAROFIBRE® and BAROFIBRE® C (cellulosic fiber, available from Halliburton Energy Services, Inc.); and the like; and any combination thereof.

In some embodiments, the concentration of a particulate WSM in a wellbore strengthening fluid (or drilling fluid) may range from a lower limit of about 0.01 pounds per barrel ("PPB"), 0.05 PPB, 0.1 PPB, 0.5 PPB, 1 PPB, 3 PPB, 5 PPB, 10 PPB, 25 PPB, or 50 PPB to an upper limit of about 150 PPB, 100 PPB, 75 PPB, 50 PPB, 25 PPB, 10 PPB, 5 PPB, 4 PPB, 3 PPB, 2 PPB, 1 PPB, or 0.5 PPB, and wherein the particulate WSM concentration may range from any lower limit to any upper limit and encompass any subset therebetween. In some embodiments, the concentration of a fiber WSM in a wellbore strengthening fluid (or drilling fluid) may range from a lower limit of about 0.01 PPB, 0.05 PPB, 0.1 PPB, 0.5 PPB, 1 PPB, 3 PPB, 5 PPB, or 10 PPB to an upper limit of about 120 PPB, 100 PPB, 75 PPB, 50 PPB, 20 PPB, 10 PPB, 5 PPB, 4 PPB, 3 PPB, 2 PPB, 1 PPB, or 0.5 PPB, and wherein the fiber WSM concentration may range from any lower limit to any upper limit and encompass any subset therebetween. One skilled in the art, with the benefit of this disclosure, should understand that the concentrations of the particulate and/or fiber WSM can effect the viscosity of the wellbore strengthening fluid, and therefore should be adjusted to ensure proper delivery of said particulate and/or fiber WSM into the wellbore.

Suitable fluids for suspending WSM and suitable base fluids for use in conjunction with the present invention may comprise oil-based fluids, aqueous-based fluids, aqueous-miscible fluids, water-in-oil emulsions, or oil-in-water emulsions. Suitable oil-based fluids may include alkanes, olefins, aromatic organic compounds, cyclic alkanes, paraffins, diesel fluids, mineral oils, desulfurized hydrogenated kerosenes, and any combination thereof. Suitable aqueous-based fluids may include fresh water, saltwater (e.g., water containing one or more salts dissolved therein), brine (e.g., saturated salt water), seawater, and any combination thereof. Suitable aqueous-miscible fluids may include, but not be limited to, alcohols, e.g., methanol, ethanol, n-propanol, isopropanol, n-butanol, sec-butanol, isobutanol, and t-butanol; glycerins; glycols, e.g., polyglycols, propylene glycol, and ethylene glycol; polyglycol amines; polyols; any derivative thereof; any in combination with salts, e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, potassium carbonate, and any combination thereof; any in combination with an aqueous-based fluid; and any combination thereof. Suitable water-in-oil emulsions, also known as invert emulsions, may have an oil-to-water ratio from a lower limit of greater than about 50:50, 55:45, 60:40, 65:35, 70:30, 75:25, or 80:20 to an upper limit of less than about 100:0, 95:5, 90:10, 85:15, 80:20, 75:25, 70:30, or 65:35 by volume in the base treatment fluid, where the amount may range from any lower limit to any upper limit and encompass any subset therebetween. Examples of suitable invert emulsions include those disclosed in U.S. Pat. Nos. 5,905,061, 5,977,031, and 6,828,279, each of which are incorporated herein by reference. It should be noted that for water-in-oil and oil-in-water emulsions, any mixture of the above may be used including the water being an aqueous-miscible fluid.

In some embodiments, a wellbore strengthening fluid (or a drilling fluid) may optionally comprise a polar organic molecule. In some embodiments, the addition of a polar organic molecule to an oil-based fluid may advantageously increase the efficacy of the WSM therein. Polar organic molecules may be any molecule with a dielectric constant greater than about 2, e.g., diethyl ether (dielectric constant of 4.3), ethyl amine (dielectric constant of 8.7), pyridine (dielectric constant of 12.3), and acetone (dielectric constant of 20.7). Polar organic molecules suitable for use in the present invention may include any polar organic molecule including protic and aprotic organic molecules. Suitable protic molecules may include, but not be limited to, organic molecules with at least one functional group to include alcohols, aldehydes, acids, amines, amides, thiols, and any combination thereof. Suitable aprotic molecules may include, but not be limited to, organic molecules with at least one functional group to include esters, ethers, nitrites, nitriles, ketones, sulfoxides, halogens, and any combination thereof. Suitable polar organic molecules may be cyclic compounds including, but not limited to, pyrrole, pyridine, furan, any derivative thereof, and any combination thereof. Suitable polar organic molecules may include an organic molecule with multiple functional groups including mixtures of protic and aprotic groups. In some embodiments, a drilling fluid may comprise multiple polar organic molecules. In some embodiments, a polar organic molecule may be present in a wellbore strengthening fluid (or a drilling fluid) in an amount from a lower limit of about 0.01%, 0.1%, 0.5%, 1%, 5%, or 10% to an upper limit of about 100%, 90%, 75%, 50%, 25%, 20%, 15%, 10%, 5%, 1%, 0.5%, or 0.1% by volume of the wellbore strengthening fluid (or the drilling fluid), and wherein the polar organic molecule concentration may range from any lower limit to any upper limit and encompass any subset therebetween.

In some embodiments, other additives may optionally be included in wellbore strengthening fluids (or drilling fluids). Examples of such additives may include, but are not limited to, salts, weighting agents, inert solids, fluid loss control agents, emulsifiers, dispersion aids, corrosion inhibitors, emulsion thinners, emulsion thickeners, viscosifying agents, surfactants, particulates, proppants, lost circulation materials, pH control additives, foaming agents, breakers, biocides, crosslinkers, stabilizers, chelating agents, scale inhibitors, gas, mutual solvents, oxidizers, reducers, and any combination thereof. A person of ordinary skill in the art, with the benefit of this disclosure, will recognize when an additive should be included in a wellbore strengthening fluid and/or drilling fluid, as well as an appropriate amount of said additive to include.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A tool comprising:
   an implement that comprises a wall having an inner surface and an outer surface, wherein an insert is disposed along the inner surface defining at least one passageway that models an opening in a subterranean formation, the passageway comprising an entry port on a first end of an object, an exit port at an opposing end of the object, and the wall extending from the entry port to the exit port, wherein a distance between opposing walls defining the passageway is adjustable; and
   at least one sensor in or on the implement wherein at least a portion of the at least one sensor is disposed on the insert proximal to the inner surface of the wall of the implement defining the passageway;
   wherein the implement comprises a holder and a multilayer insert capable of operably mating with a holder, and wherein the multilayer insert comprises the at least one sensor.

2. The tool of claim 1, wherein the at least one sensor is selected from the group consisting of a force gauge, a load cell, a piezoelectric sensor, a magnetic sensor, an ultrasonic sensor, and a strain gauge.

3. The tool of claim 1, wherein the at least one sensor is embedded in the implement.

4. The tool of claim 1, wherein the at least one sensor is disposed on the wall of the passageway.

5. The tool of claim 1, wherein the passageway has at least one adjustable wall.

6. The tool of claim 1, wherein the passageway is a tapered slot passageway with the entry port has a smallest dimension between about 1000 microns and about 6000 microns, the exit port with a smallest dimension between about 100 microns and about 3000 microns, and the smallest dimension of the exit port is less than the smallest dimension of the entry port.

7. The tool of claim 1, wherein the entry port and the exit port have a slit shape.

8. The tool of claim 1, wherein the entry port and the exit port have a shape of an artificial or man-made fracture.

9. The tool of claim 1, wherein the passageway is a natural fracture in a core sample.

10. A tool comprising:
    an implement that comprises a tapered slot that models an opening in a subterranean formation, a passageway comprising an entry port having a slit shape with a smallest dimension between about 1000 microns and about 6000 microns on a first end of an object, an exit port having a slit shape with a smallest dimension between about 100 microns and about 3000 microns at an opposing end of the object, and a wall extending from the entry port to the exit port, wherein an insert is disposed along an inner wall surface, wherein the smallest dimension of the exit port is less than the smallest dimension of the entry port; and
    at least one sensor in or on the implement wherein at least a portion of the at least one sensor is disposed on the insert proximal to the wall of the passageway;
    wherein the implement comprises a holder and a multilayer insert capable of operably mating with a holder, and wherein the multilayer insert comprises the at least one sensor.

11. The tool of claim 10, wherein the at least one sensor is selected from the group consisting of a force gauge, a load cell, a piezoelectric sensor, a magnetic sensor, an ultrasonic sensor, and a strain gauge.

12. The tool of claim 10, wherein the at least one sensor is embedded in the implement.

13. The tool of claim 10, wherein the at least one sensor is disposed on the wall of the passageway.

14. The tool of claim 10, wherein the passageway has at least one adjustable wall.

* * * * *